(12) United States Patent
Paschalides et al.

(10) Patent No.: US 9,145,420 B1
(45) Date of Patent: Sep. 29, 2015

(54) CRYSTALLINE FORMS OF MORPHINE SULFATE

(71) Applicant: Johnson Matthey Public Limited Company, London (GB)

(72) Inventors: Nicholas D. Paschalides, Marlborough, MA (US); Mahmoud Mirmehrabi, Halifax (CA)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 14/670,493

(22) Filed: Mar. 27, 2015

(51) Int. Cl.
*A61K 31/485* (2006.01)
*C07D 489/04* (2006.01)

(52) U.S. Cl.
CPC ........... *C07D 489/04* (2013.01); *C07B 2200/13* (2013.01)

(58) Field of Classification Search
USPC ............................................. 514/282; 546/44
See application file for complete search history.

(56) References Cited

U.S. PATENT DOCUMENTS

| 5,202,128 A | 4/1993 | Morella et al. |
| 5,215,758 A | 6/1993 | Krishnamurthy |
| 5,378,474 A | 1/1995 | Morella et al. |
| 5,672,360 A | 9/1997 | Sackler et al. |
| 2014/0275146 A1 | 9/2014 | Marmor |

*Primary Examiner* — Charanjit Aulakh

(57) ABSTRACT

The present disclosure is directed to crystalline forms of morphine sulfate and pharmaceutical compositions comprising any of the crystalline forms of morphine sulfate. Also provided are processes for the preparation of crystalline forms of morphine sulfate.

19 Claims, 18 Drawing Sheets

CRYSTALLINE FORMS OF MORPHINE SULFATE

FIELD OF THE INVENTION

The present disclosure relates to crystalline forms of morphine sulfate, and methods for making the same. The present disclosure also relates to pharmaceutical compositions containing morphine sulfate and methods for treating pain using such compositions.

BACKGROUND OF THE INVENTION

Morphine is the most abundant of at least 50 alkaloids found in opium, poppy and poppy derivatives, *Papaver somniferum*. Poppy straw is opium poppy (*Poppy somniferum*) that is harvested when fully mature and dry, minus the ripe poppy seeds. An agricultural by-product of the poppy seed harvest, the straw was a waste product before the 1930s when a chemical process became available to extract morphine from it. Poppy straw consisting mainly of the capsule became a valuable source of morphine. Today, poppy straw is a major source of many opioids and other alkaloids. It is the source of 90% of the world supply of legal morphine (i.e. for medical and scientific use).

During processing, poppy straw is pulverized and washed many times in water and/or various acids and other chemicals to produce poppy straw concentrate (PSC) or concentrated poppy straw (CPS). Once dried, the concentrate is a beige to brown colored powder and contains salts of various alkaloids. It can range from about 9 to 30 times the morphine concentration of poppy straw. Morphine is generally 8% to 17% of the dry weight of opium, although specially-designed cultivars reach 26% or produce little morphine at all. The latter varieties, including the Przemko and Norman strains of the opium poppy, are used to produce two other alkaloids, thebaine and oripavine, which are used in the manufacture of semi-synthetic opioids like oxycodone and etorphine as well as other types of drugs. At least one manufacturer, Tasmanian Alkaloids, produces both high-morphine and high-thebaine/oripavine types of CPS.

Morphine is produced most predominantly early in the life cycle of the plant and, past the optimum point for extraction, various processes in the plant produce codeine, thebaine, and in some cases low quantities of hydromorphone, dihydromorphine, dihydrocodeine, tetrahydrothebaine and hydrocodone.

Morphine, generally administered in a salt form, is a potent opiate analgesic, for the relief of moderate to severe pain, and has been approved for use for decades. It can be administered as an injectable solution, suppository, capsule, tablet or extended release product. Like other opioids, e.g. oxycodone, hydromorphone and diacetylmorphine (heroin), morphine acts directly on the central nervous system (CNS) to relieve pain. Today, morphine sulfate is sold under various trade names including Astramorph PF™, Avinza®, DepoDur®, Duramorph, Infumorph, Kadian®, MS-Contin®, Oramorph® SR and RMS. Kadian® is a morphine sustained-release dosage form for once or twice per day dosing. Kadian® is currently available in 10, 20, 30, 40, 50, 60, 80, 100 and 200 mg morphine sulfate extended release capsules.

Morphine is regarded as the opioid drug of choice in the treatment of cancer pain, for example. Side effects of morphine treatment include, for example, nausea and vomiting, constipation, sedation, confusion and loss of appetite. It has been suggested that the use of modified release morphine formulations, apart from their convenience and their ability to provide continuous analgesia, may also result in a lower incidence and severity of morphine-related side effects. Sustained-release morphine dosage forms are described in U.S. Pat. Nos. 5,202,128, 5,215,758, 5,378,474 and 5,672,360.

All references cited herein, including the morphine sulfate products associated with the above-mentioned trade names, are incorporated herein by reference in their entireties.

SUMMARY OF THE INVENTION

The present disclosure is directed to eight novel crystalline forms of morphine sulfate. These forms are identified herein as Forms $\alpha$, $\beta$, $\gamma$, $\delta$, $\epsilon$, $\zeta$, $\eta$ and $\theta$. The present disclosure is further directed to processes for the preparation of the crystalline forms of morphine sulfate as herein described.

Illustrative of the present disclosure is a pharmaceutical composition comprising at least one pharmaceutically acceptable excipient and any of the crystalline forms of morphine sulfate as herein described. An illustration of the present disclosure is a pharmaceutical composition made by mixing any of the crystalline forms of morphine sulfate as herein described and at least one pharmaceutically acceptable excipient. Illustrating the present disclosure is a process for making a pharmaceutical composition comprising mixing any of the crystalline forms of morphine sulfate as herein described and at least one pharmaceutically acceptable excipient.

Exemplifying the present disclosure are methods of treating pain, comprising administering to a subject in need thereof, one or more of the morphine sulfate crystalline forms or pharmaceutical compositions described above.

DETAILED DESCRIPTION OF THE INVENTION

Figure 1:
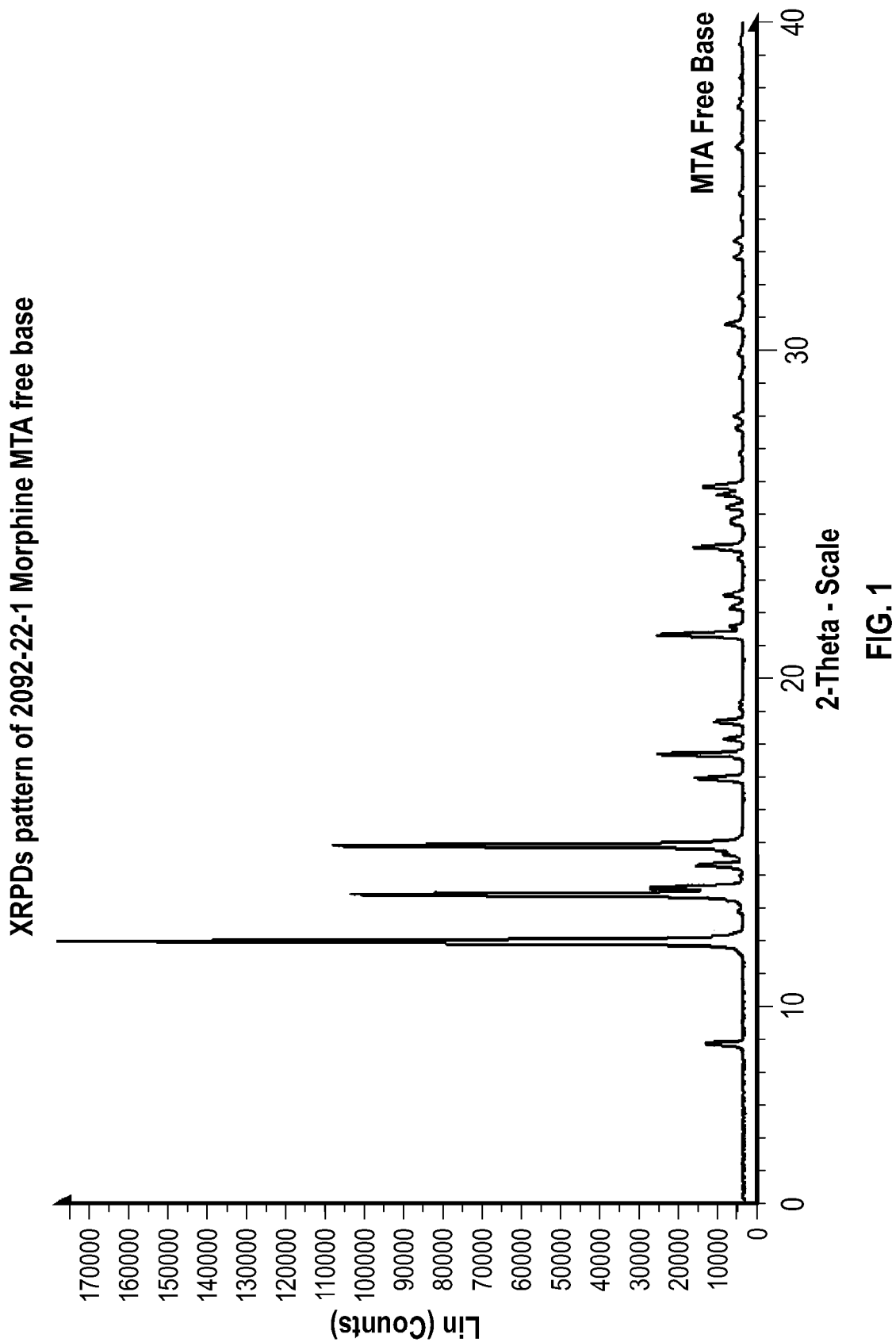
FIG. 1 is an X-ray powder diffractogram of morphine free base, expressed in terms of °2θ.

The present disclosure is directed to eight novel crystalline forms of morphine sulfate, as herein described in detail. More particularly, the present disclosure is directed to novel crystalline Forms α, β, γ, δ, ε, ζ, η and θ of morphine sulfate.

The present disclosure is further directed to processes for the preparation of the crystalline forms of morphine sulfate, as described in more detail in the Examples which follow herein.

The present disclosure is further directed to pharmaceutical compositions comprising one or more of the crystalline forms of morphine sulfate. The present disclosure is further directed to a method of treating pain comprising administering to a subject in need thereof, one or more of the forms of morphine sulfate.

The term "composition" as used herein is intended to encompass a product comprising the specified ingredients in the specified amounts, as well as any product which results, directly or indirectly, from combinations of the specified ingredients in the specified amounts.

The term "excipient" as used herein refers to a pharmaceutically acceptable organic or inorganic carrier substance. Excipients may be natural or synthetic substances formulated alongside the active ingredient of a medication, included for the purpose of bulking-up formulations that contain potent active ingredients (thus often referred to as "bulking agents," "fillers," or "diluents"), or to confer a therapeutic enhancement on the active ingredient in the final dosage form, such as facilitating drug absorption or solubility. Excipients can also be useful in the manufacturing process, to aid in the handling of the active substance, such as by facilitating powder flowability or non-stick properties, in addition to aiding in vitro stability such as prevention of denaturation over the expected shelf life.

The term "subject" as used herein refers to an animal, preferably a mammal, most preferably a human, who has been the object of treatment, observation or experiment. Preferably, the subject has experienced and/or exhibited at least one symptom of the disease or disorder to be treated and/or prevented. Further, a subject may not have exhibited any symptoms of the disorder, disease or condition to be treated and/or prevented, but has been deemed by a physician, clinician or other medical professional to be at risk for developing said disorder, disease or condition.

The terms "treating," "treatment" and the like as used herein shall include the management and care of a subject (preferably a mammal, more preferably a human) for the purpose of combating a disease, condition, or disorder and includes the administration of a compound of the present disclosure to prevent the onset of the symptoms or complications, alleviate the symptoms or complications, or eliminate the disease, condition, or disorder.

The crystalline forms of morphine sulfate of the present disclosure may be prepared directly or indirectly from morphine free base. Examples 1-10, which follow herein, provide embodiments of the preparation of the crystalline forms of morphine sulfate.

The crystalline forms of morphine sulfate herein described may be characterized by one or more of their characteristic physical properties including, but not limited to, X-ray powder diffraction peaks and differential scanning calorimetry.

The crystalline forms of morphine sulfate may be identified by their X-ray powder diffraction peaks/pattern. X-ray powder diffraction analysis on representative samples of the crystalline forms of morphine sulfate as herein described is performed using a Bruker D8 Advance instrument equipped with a Cu Kα radiation source (1.54° Angstrom), a 9-position sample holder and a LYNXEYE™ Super Speed Detector. Samples are placed on zero-background, silicon plate holders.

One skilled in the art would recognize that the ° 2θ values and the relative intensity values are generated by performing a peak search on the measured data and the d-spacing values are calculated by the instrument from the ° 2θ values using Bragg's equation. One skilled in the art would further recognize that the relative intensity for the measured peaks may vary as a result of sample preparation, orientation and instrument used, for example. A variation of about ±0.2 is not atypical in obtainable 2θ values.

Figure 2:
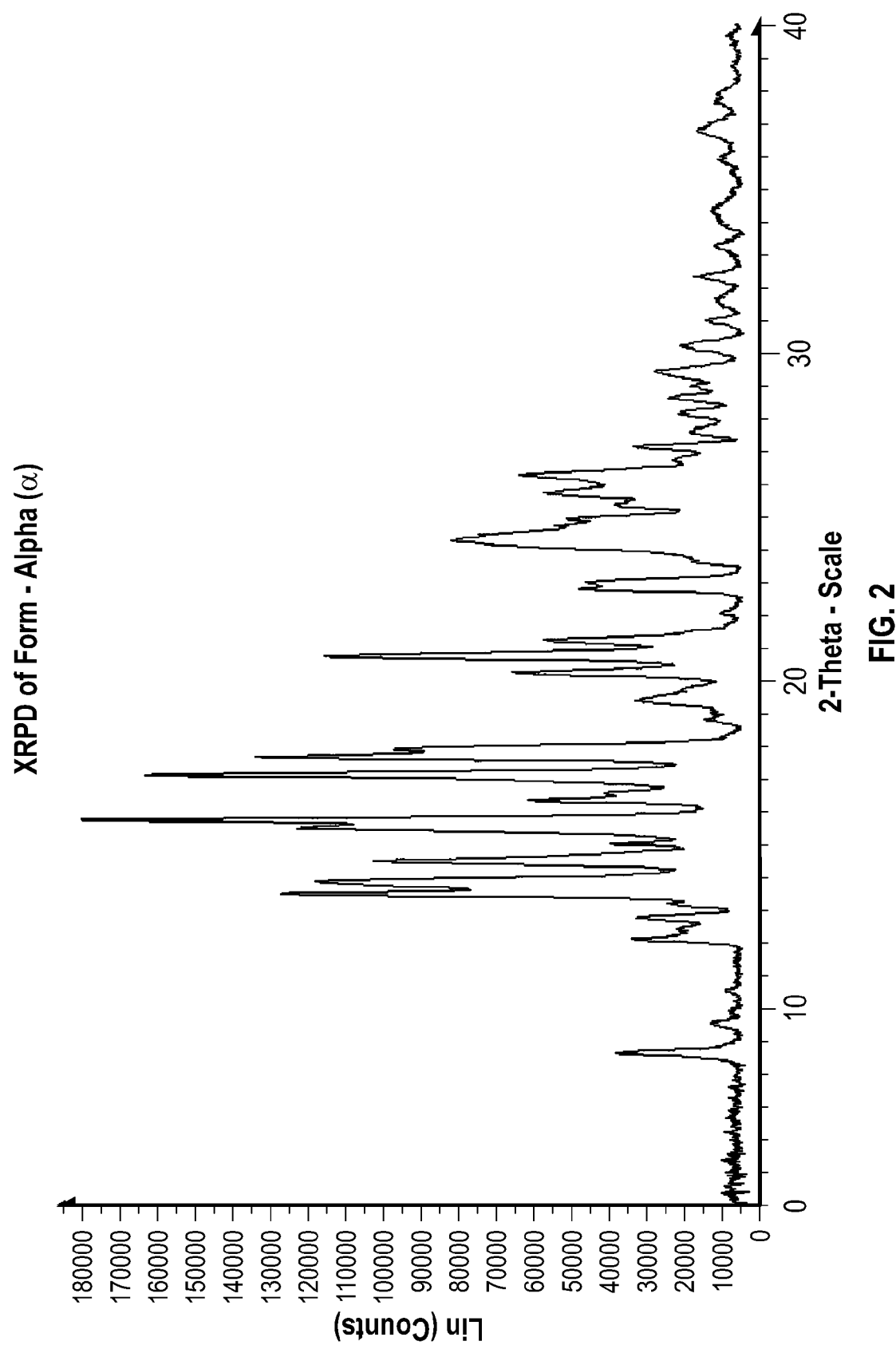
FIG. 2 is an X-ray powder diffractogram of morphine sulfate crystalline Form $\alpha$, expressed in terms of °2θ.

Morphine sulfate Form α is a unique crystalline phase. Morphine sulfate Form α may be characterized as a white to off-white powder. Morphine sulfate Form α is further characterized by its X-ray powder diffraction pattern peaks and/or d-spacing values, as listed in Table 1 below. FIG. 2 is a representative X-ray powder diffractogram for a representative sample of morphine sulfate Form α made according to Examples 3 and 4.

TABLE 1

XRPD peak list of Form α

| 2θ | d spacing, A° | Count | % |
|---|---|---|---|
| 7.54 | 11.721 | 7785 | 4.3 |
| 8.61 | 10.268 | 38031 | 21.1 |
| 9.49 | 9.312 | 12778 | 7.1 |
| 9.85 | 8.973 | 7574 | 4.2 |
| 10.49 | 8.429 | 8583 | 4.8 |
| 12.07 | 7.328 | 33865 | 18.7 |
| 12.72 | 6.954 | 32689 | 18.1 |
| 13.14 | 6.735 | 24265 | 13.4 |
| 13.45 | 6.576 | 127441 | 70.6 |
| 13.81 | 6.405 | 116666 | 64.6 |
| 14.45 | 6.125 | 102448 | 56.7 |
| 14.98 | 5.908 | 39629 | 21.9 |
| 15.48 | 5.721 | 123015 | 68.1 |
| 15.71 | 5.635 | 180619 | 100 |
| 16.32 | 5.429 | 61348 | 34 |
| 16.53 | 5.360 | 41019 | 22.7 |
| 17.08 | 5.187 | 163643 | 90.6 |
| 17.63 | 5.026 | 134116 | 74.3 |
| 17.86 | 4.964 | 97291 | 53.9 |
| 18.78 | 4.721 | 13223 | 7.3 |
| 19.36 | 4.581 | 32796 | 18.2 |
| 19.69 | 4.506 | 20822 | 11.5 |
| 20.20 | 4.394 | 65519 | 36.3 |
| 20.71 | 4.286 | 115491 | 63.9 |
| 21.19 | 4.190 | 57204 | 31.7 |
| 22.03 | 4.032 | 10157 | 5.6 |
| 22.94 | 3.874 | 46005 | 25.5 |
| 23.63 | 3.762 | 18021 | 10 |
| 24.24 | 3.669 | 82081 | 45.4 |
| 24.88 | 3.575 | 50940 | 28.2 |
| 25.32 | 3.514 | 38533 | 21.3 |
| 25.69 | 3.466 | 57300 | 31.7 |
| 26.22 | 3.396 | 63972 | 35.4 |
| 26.70 | 3.336 | 13001 | 12.7 |
| 27.09 | 3.289 | 33408 | 18.5 |
| 27.55 | 3.235 | 18065 | 10 |
| 28.12 | 3.171 | 21428 | 11.9 |
| 28.59 | 3.120 | 23902 | 13.2 |
| 28.94 | 3.083 | 17979 | 10 |
| 29.37 | 3.039 | 27704 | 15.3 |
| 30.17 | 2.960 | 21079 | 11.7 |
| 30.93 | 2.889 | 14141 | 7.8 |
| 31.54 | 2.834 | 11195 | 6.2 |
| 32.27 | 2.772 | 17448 | 9.7 |
| 33.212 | 2.69534 | 11463 | 6.3 |

TABLE 1-continued

XRPD peak list of Form α

| 2θ | d spacing, A° | Count | % |
|---|---|---|---|
| 33.974 | 2.63664 | 10917 | 6 |
| 34.293 | 2.61282 | 12547 | 6.9 |
| 35.837 | 2.50371 | 10904 | 6 |
| 36.722 | 2.4454 | 16439 | 9.1 |
| 37.636 | 2.38808 | 11620 | 6.4 |
| 37.839 | 2.37569 | 11178 | 6.2 |
| 39.62 | 2.27295 | 7555 | 4.2 |

Figure 3:
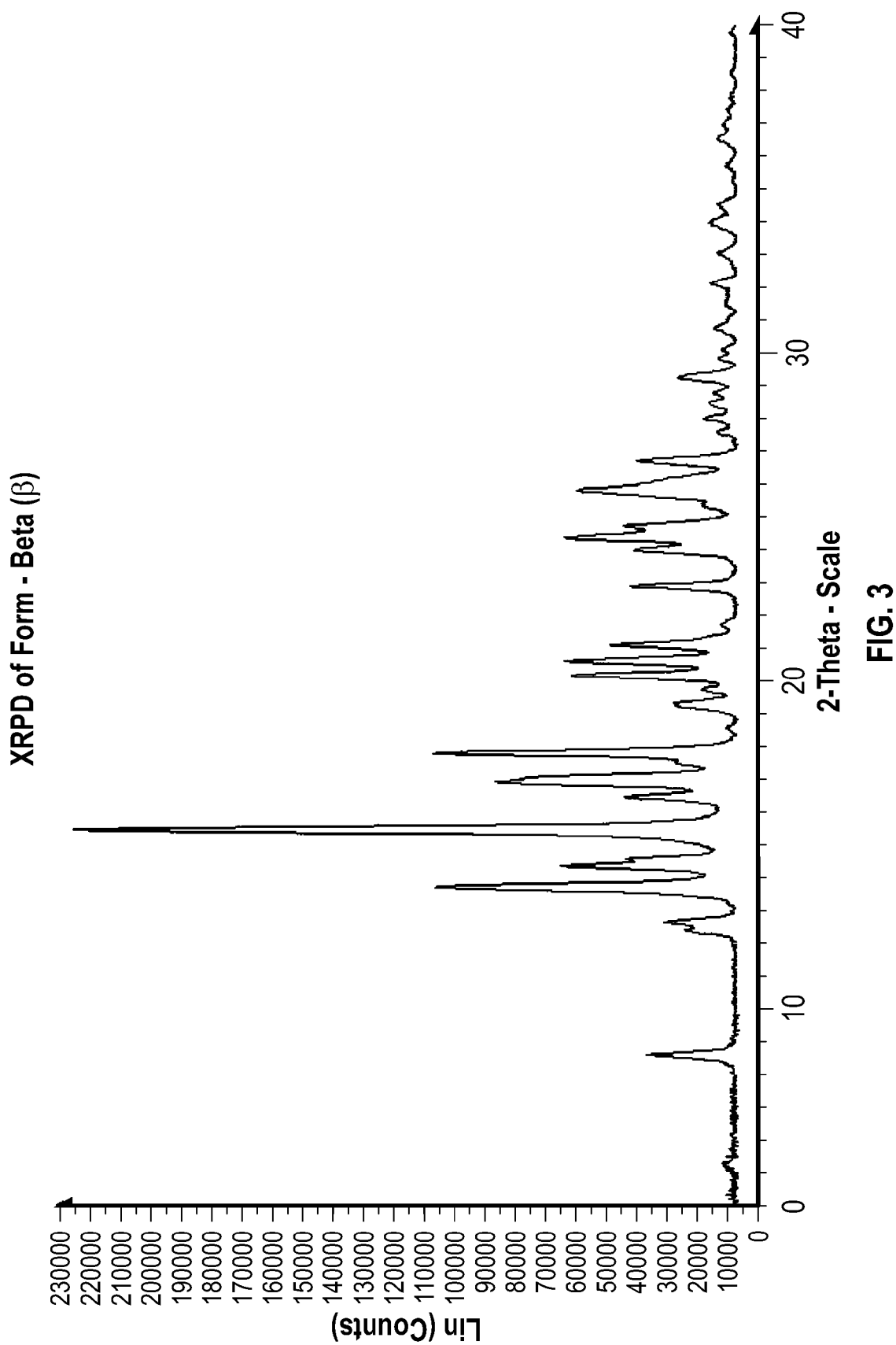
FIG. 3 is an X-ray powder diffractogram of morphine sulfate crystalline Form $\beta$, expressed in terms of °2θ.

Morphine sulfate Form β is a unique crystalline phase. Morphine sulfate Form β may be characterized as a white to off-white powder. Morphine sulfate Form β is further characterized by its X-ray powder diffraction pattern peaks and/or d-spacing values, as listed in Table 2 below. FIG. 3 is a representative X-ray powder diffractogram for a representative sample of morphine sulfate Form β made according to Example 5.

TABLE 2

XRPD peak list of Form β

| 2θ | d spacing, A° | Count | % |
|---|---|---|---|
| 5.21 | 16.962 | 9073 | 5 |
| 8.56 | 10.322 | 26160 | 14.5 |
| 12.36 | 7.156 | 18702 | 10.4 |
| 12.60 | 7.020 | 23369 | 12.9 |
| 13.68 | 6.468 | 80427 | 44.5 |
| 14.32 | 6.178 | 49082 | 27.2 |
| 14.52 | 6.094 | 33095 | 18.3 |
| 15.43 | 5.738 | 180661 | 100 |
| 16.42 | 5.394 | 35816 | 19.8 |
| 16.89 | 5.246 | 68594 | 38 |
| 17.78 | 4.984 | 82044 | 45.4 |
| 18.55 | 4.779 | 8643 | 4.8 |
| 19.26 | 4.605 | 22015 | 12.2 |
| 19.72 | 4.499 | 15094 | 8.4 |
| 20.14 | 4.406 | 49433 | 27.4 |
| 20.58 | 4.313 | 50985 | 28.2 |
| 21.08 | 4.212 | 37666 | 2.0.8 |
| 21.67 | 4.097 | 10205 | 5.6 |
| 22.87 | 3.886 | 31679 | 17.5 |
| 23.98 | 3.709 | 31482 | 17.4 |
| 24.34 | 3.653 | 49142 | 27.2 |
| 24.69 | 3.603 | 35649 | 19.7 |
| 25.34 | 3.512 | 14993 | 8.3 |
| 25.78 | 3.453 | 48874 | 27.1 |
| 26.13 | 3.407 | 26087 | 14.4 |
| 26.68 | 3.339 | 33491 | 18.5 |
| 27.58 | 3.232 | 11169 | 6.2 |
| 27.99 | 3.185 | 13749 | 7.6 |
| 28.43 | 3.136 | 12380 | 6.9 |
| 28.75 | 3.102 | 11857 | 6.6 |
| 29.25 | 3.051 | 21413 | 11.9 |
| 29.81 | 2.995 | 10374 | 5.7 |
| 30.75 | 2.906 | 11393 | 6.3 |
| 31.50 | 2.837 | 8816 | 4.9 |
| 32.10 | 2.786 | 12678 | 7 |
| 33.02 | 2.710 | 10467 | 5.8 |
| 33.94 | 2.639 | 12603 | 7 |
| 34.50 | 2.598 | 10964 | 6.1 |
| 35.69 | 2.513 | 8555 | 4.7 |
| 36.56 | 2.456 | 10659 | 5.9 |

Figure 4:
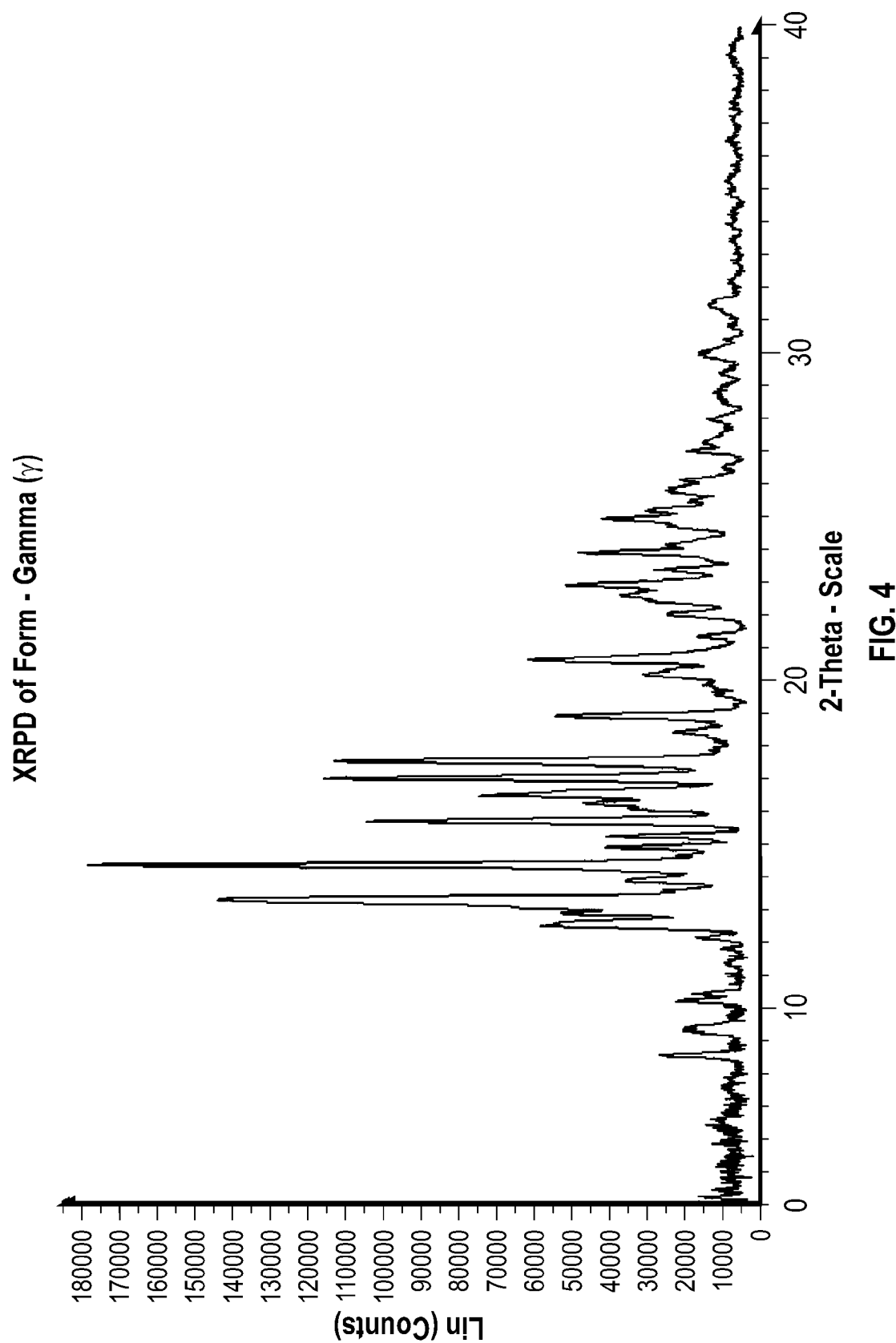
FIG. 4 is an X-ray powder diffractogram of morphine sulfate crystalline Form $\gamma$, expressed in terms of °2θ.

Morphine sulfate Form γ is a unique crystalline phase. Morphine sulfate Form γ may be characterized as a white to off-white powder. Morphine sulfate Form γ is further characterized by its X-ray powder diffraction pattern peaks and/or d-spacing values, as listed in Table 3 below. FIG. 4 is a representative X-ray powder diffractogram for a representative sample of morphine sulfate Form γ made according to Example 6.

TABLE 3

XRPD peak list of Form γ

| 2θ | d spacing, A° | Count | % |
|---|---|---|---|
| 7.453 | 11.852 | 14058 | 7.6 |
| 8.455 | 10.450 | 30831 | 16.6 |
| 9.269 | 9.534 | 24458 | 13.2 |
| 10.115 | 8.738 | 26802 | 14.4 |
| 10.333 | 8.554 | 22449 | 12.1 |
| 11.274 | 7.842 | 13683 | 7.4 |
| 11.716 | 7.547 | 14746 | 7.9 |
| 12.049 | 7.340 | 21602 | 11 6 |
| 12.457 | 7.100 | 63642 | 34.3 |
| 12.804 | 6.908 | 58128 | 31.3 |
| 13.214 | 6.695 | 150759 | 81.2 |
| 13.811 | 6.407 | 40814 | 22 |
| 14.284 | 6.195 | 185710 | 100 |
| 14.826 | 5.970 | 46595 | 25.1 |
| 15.176 | 5.834 | 46458 | 25 |
| 15.627 | 5.666 | 110758 | 59.6 |
| 16.174 | 5.476 | 52472 | 28.3 |
| 16.445 | 5.386 | 80017 | 43.1 |
| 16.95 | 5.227 | 122648 | 66 |
| 17.467 | 5.073 | 119559 | 64.4 |
| 18.363 | 4.828 | 28359 | 15.3 |
| 18.852 | 4.703 | 59796 | 32.2 |
| 19.542 | 4.539 | 16054 | 8.6 |
| 20.129 | 4.408 | 36101 | 19.4 |
| 20.577 | 4.313 | 67254 | 36.2 |
| 21.291 | 4.170 | 21516 | 11.6 |
| 21.989 | 4.039 | 29706 | 16 |
| 22.549 | 3.940 | 42588 | 22.9 |
| 22.869 | 3.885 | 57195 | 30.8 |
| 23.329 | 3.810 | 33391 | 18 |
| 23.871 | 3.725 | 53918 | 29 |
| 24.101 | 3.690 | 30277 | 16.3 |
| 24.68 | 3.604 | 29904 | 16.1 |
| 24.903 | 3.573 | 47681 | 25.7 |
| 25.157 | 3.537 | 35556 | 19.1 |
| 25.758 | 3.456 | 30234 | 16.3 |
| 26.09 | 3.413 | 26587 | 14.3 |
| 26.474 | 3.364 | 15218 | 8.2 |
| 26.992 | 3.301 | 24641 | 13.3 |
| 27.243 | 3.271 | 19820 | 10.7 |
| 27.944 | 3.190 | 18586 | 10 |
| 28.632 | 3.115 | 15926 | 8.6 |
| 29.37 | 3.039 | 15433 | 8.3 |
| 29.953 | 2.981 | 20227 | 10.9 |
| 30.801 | 2.901 | 13006 | 7 |
| 31.443 | 2.843 | 18739 | 10.1 |

Figure 5:
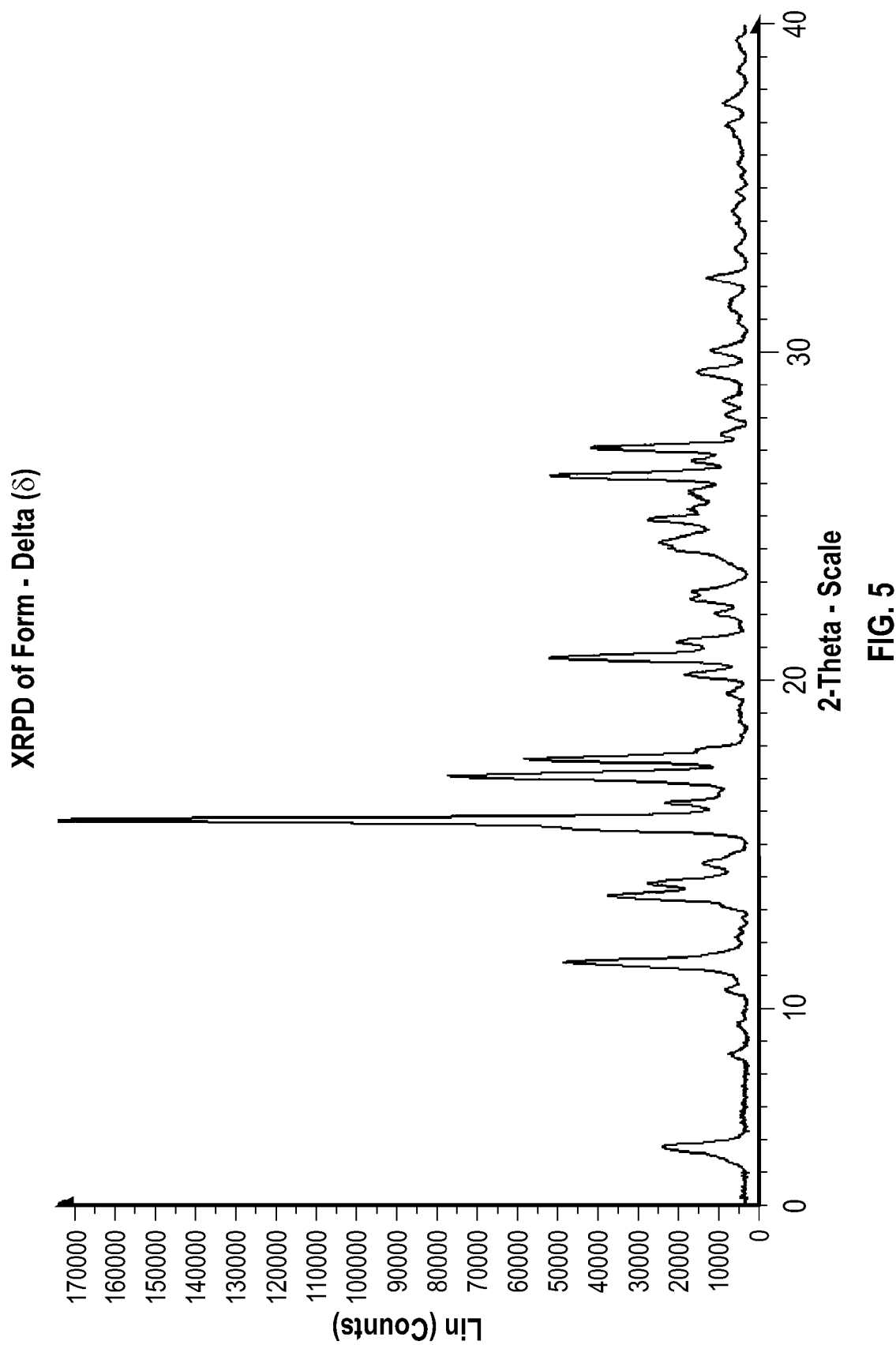
FIG. 5 is an X-ray powder diffractogram of morphine sulfate crystalline Form $\delta$, expressed in terms of °2θ.

Morphine sulfate Form δ is a unique crystalline phase. Morphine sulfate Form δ may be characterized as a white to off-white powder. Morphine sulfate Form δ is further characterized by its X-ray powder diffraction pattern peaks and/or d-spacing values, as listed in Table 4 below. FIG. 5 is a representative X-ray powder diffractogram for a representative sample of morphine sulfate Form δ made according to Example 7.

TABLE 4

XRPD peak list of Form δ

| 2θ | d spacing, A° | Count | % |
|---|---|---|---|
| 5.70 | 15.486 | 23544 | 13.3 |
| 8.54 | 10.344 | 7313 | 4.1 |
| 9.43 | 9.368 | 5049 | 2.9 |
| 10.50 | 8.416 | 8086 | 4.6 |
| 11.34 | 7.799 | 48561 | 27.5 |
| 13.37 | 6.615 | 37282 | 21.1 |
| 13.76 | 6.432 | 27356 | 15.5 |
| 14.37 | 6.159 | 13851 | 7.8 |
| 15.39 | 5.754 | 44927 | 25.4 |
| 15.68 | 5.646 | 176656 | 100 |

TABLE 4-continued

XRPD peak list of Form δ

| 2θ | d spacing, A° | Count | % |
|---|---|---|---|
| 16.20 | 5.466 | 23125 | 13.1 |
| 17.03 | 5.203 | 77012 | 43.6 |
| 17.54 | 5.051 | 58036 | 32.9 |
| 17.87 | 4.961 | 14950 | 8.5 |
| 19.55 | 4.537 | 7832 | 4.4 |
| 20.14 | 4.406 | 18108 | 10.3 |
| 20.64 | 4.299 | 52029 | 29.5 |
| 21.15 | 4.198 | 20217 | 11.4 |
| 21.99 | 4.03875 | 10728 | 6.1 |
| 22.427 | 3.96113 | 16914 | 9.6 |
| 22.66 | 3.92087 | 16607 | 9.4 |
| 24.001 | 3.70482 | 22324 | 12.6 |
| 24.169 | 3.6794 | 24531 | 13.9 |
| 24.873 | 3.57683 | 27399 | 15.5 |
| 25.184 | 3.53337 | 17641 | 10 |
| 25.71 | 3.46233 | 17253 | 9.8 |
| 26.202 | 3.39833 | 51837 | 29.3 |
| 26.659 | 3.34116 | 16594 | 9.4 |
| 27.052 | 3.2935 | 41688 | 23.6 |
| 27.477 | 3.24353 | 9229 | 5.2 |
| 28.06 | 3.17744 | 8234 | 4.7 |
| 28.488 | 3.13069 | 8906 | 5 |
| 29.37 | 3.03856 | 15075 | 8.5 |
| 30.03 | 2.97327 | 11893 | 6.7 |
| 31.512 | 2.83673 | 6770 | 3.8 |
| 32.238 | 2.77452 | 12699 | 7.2 |
| 33.137 | 2.70129 | 5857 | 3.3 |
| 34.866 | 2.57114 | 5473 | 3.1 |
| 35.732 | 2.51081 | 5019 | 2.8 |
| 36.913 | 2.43317 | 7795 | 4.4 |
| 37.581 | 2.39145 | 8745 | 5 |
| 38.562 | 2.33282 | 5063 | 2.9 |
| 39.5 | 2.27953 | 5249 | 3 |

Figure 6:
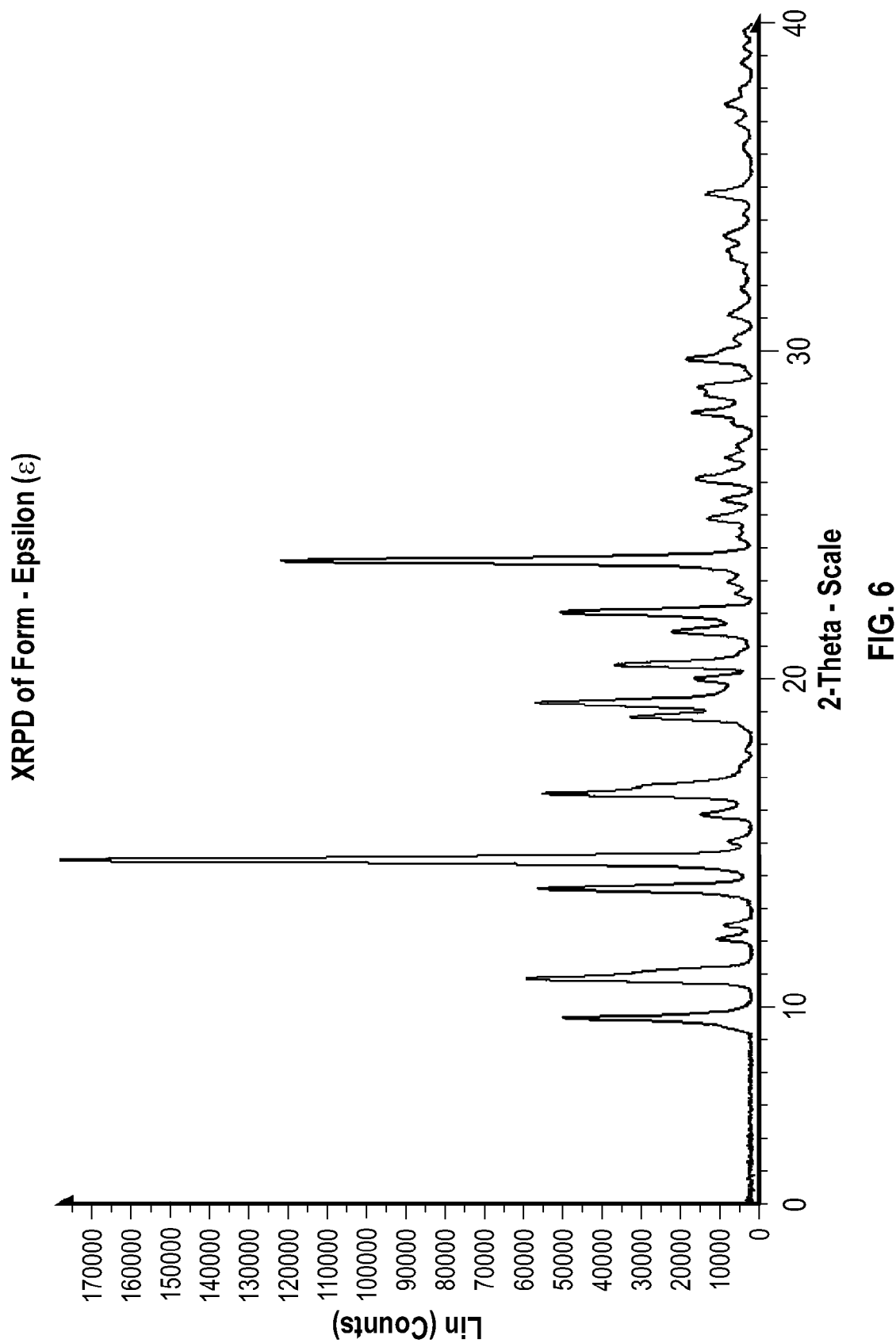
FIG. 6 is an X-ray powder diffractogram of morphine sulfate crystalline Form $\epsilon$, expressed in terms of °2θ.

Morphine sulfate Form ε is a unique crystalline phase. Morphine sulfate Form ε may be characterized as a white to off-white powder. Morphine sulfate Form ε is further characterized by its X-ray powder diffraction pattern peaks and/or d-spacing values, as listed in Table 5 below. FIG. 6 is a representative X-ray powder diffractogram for a representative sample of morphine sulfate Form ε made according to Example 8.

TABLE 5

XRPD peak list of Form ε

| 2θ | d spacing, A° | Count | % |
|---|---|---|---|
| 9.59 | 9.216 | 19596 | 27.5 |
| 10.80 | 8.189 | 58820 | 32.6 |
| 11.03 | 8.012 | 28976 | 16 |
| 12.01 | 7.362 | 10490 | 5.8 |
| 12.41 | 7.125 | 8694 | 4.8 |
| 13.54 | 6.535 | 56197 | 31.1 |
| 14.40 | 6.145 | 180610 | 100 |
| 14.98 | 5.911 | 7730 | 4.3 |
| 15.79 | 5.608 | 15043 | 8.3 |
| 16.44 | 5.389 | 54987 | 30.4 |
| 16.67 | 5.313 | 30704 | 17 |
| 17.22 | 5.141 | 4957 | 2.7 |
| 17.78 | 4.984 | 3188 | 1.8 |
| 18.77 | 4.723 | 32612 | 18.1 |
| 19.20 | 4.620 | 56708 | 31.4 |
| 19.92 | 4.453 | 16250 | 9 |
| 20.38 | 4.355 | 36651 | 20.3 |
| 21.42 | 4.145 | 21869 | 12.1 |
| 22.01 | 4.036 | 50499 | 28 |
| 22.59 | 3.934 | 5792 | 3.2 |
| 22.94 | 3.874 | 7766 | 4.3 |
| 23.58 | 3.770 | 121785 | 67.4 |
| 24.29 | 3.661 | 5575 | 3.1 |

TABLE 5-continued

XRPD peak list of Form ε

| 2θ | d spacing, A° | Count | % |
|---|---|---|---|
| 24.87 | 3.577 | 13138 | 7.3 |
| 25.44 | 3.498 | 9570 | 5.3 |
| 26.08 | 3.414 | 16116 | 8.9 |
| 26.73 | 3.333 | 8477 | 4.7 |
| 27.10 | 3.288 | 5173 | 3 |
| 27.78 | 3.209 | 7022 | 3.9 |
| 28.09 | 3.174 | 17147 | 9.5 |
| 28.66 | 3.113 | 13869 | 7.7 |
| 28.87 | 3.090 | 15599 | 8.6 |
| 29.73 | 3.003 | 18568 | 10.3 |
| 30.35 | 2.942 | 6191 | 3.4 |
| 31.08 | 2.876 | 7841 | 4.3 |
| 31.87 | 2.806 | 4392 | 2.4 |
| 32.82 | 2.726 | 6976 | 3.9 |
| 33.03 | 2.710 | 8059 | 4.5 |
| 33.48 | 2.674 | 8999 | 5 |
| 34.77 | 2.578 | 13351 | 7.4 |
| 36.18 | 2.481 | 3929 | 2.2 |
| 36.93 | 2.432 | 5783 | 3.2 |
| 37.50 | 2.396 | 8307 | 4.6 |
| 37.93 | 2.370 | 4888 | 2.7 |
| 38.76 | 2.321 | 4425 | 2.4 |
| 39.26 | 2.293 | 3838 | 2.1 |
| 39.72 | 2.267 | 3764 | 2.1 |

Figure 7:
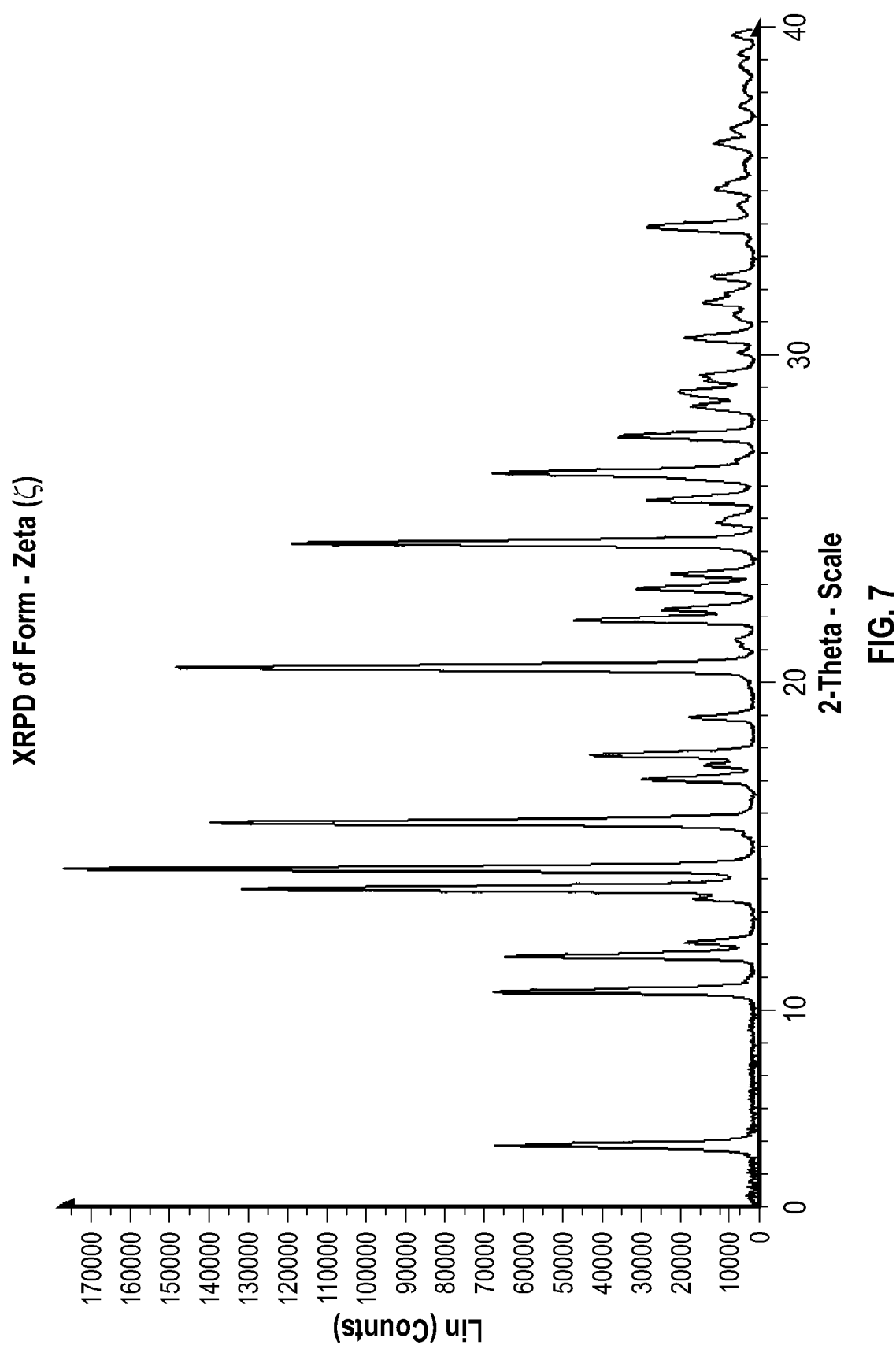
FIG. 7 is an X-ray powder diffractogram of morphine sulfate crystalline Form $\zeta$, expressed in terms of °2θ.

Morphine sulfate Form ζ is a unique crystalline phase. Morphine sulfate Form ζ may be characterized as a white to off-white powder. Morphine sulfate Form ζ is further characterized by its X-ray powder diffraction pattern peaks and/or d-spacing values, as listed in Table 6 below. FIG. 7 is a representative X-ray powder diffractogram for a representative sample of morphine sulfate Form ζ made according to Example 9.

TABLE 6

XRPD peak list of Form ζ

| 2θ | d spacing, A° | Count | % |
|---|---|---|---|
| 5.83 | 15.145 | 67066 | 37.9 |
| 10.53 | 8.397 | 67455 | 38.1 |
| 11.61 | 7.613 | 64699 | 36.6 |
| 12.03 | 7.353 | 18553 | 10.5 |
| 13.37 | 6.617 | 16740 | 9.5 |
| 13.67 | 6.475 | 131887 | 74.5 |
| 14.28 | 6.198 | 177010 | 100 |
| 15.68 | 5.646 | 139905 | 79 |
| 17.03 | 5.203 | 29597 | 16.7 |
| 17.45 | 5.078 | 13720 | 7.8 |
| 17.76 | 4.989 | 42869 | 24.2 |
| 18.93 | 4.685 | 17523 | 9.9 |
| 20.44 | 4.342 | 148314 | 83.8 |
| 21.28 | 4.173 | 5956 | 3.4 |
| 21.89 | 4.056 | 47000 | 26.6 |
| 22.24 | 3.995 | 24366 | 13.8 |
| 22.86 | 3.888 | 31247 | 17.7 |
| 23.30 | 3.815 | 22223 | 12.6 |
| 24.24 | 3.668 | 118902 | 67.2 |
| 24.89 | 3.575 | 10814 | 6.1 |
| 25.56 | 3.482 | 28441 | 16.1 |
| 26.39 | 3.374 | 67762 | 38.3 |
| 26.81 | 3.323 | 5745 | 3.2 |
| 27.52 | 3.239 | 35467 | 20 |
| 28.44 | 3.136 | 17251 | 9.7 |
| 28.87 | 3.091 | 20379 | 11.5 |
| 29.26 | 3.049 | 12317 | 7 |
| 30.08 | 2.968 | 5088 | 2.9 |
| 30.52 | 2.927 | 18570 | 10.5 |
| 31.22 | 2.862 | 6028 | 3.4 |
| 31.62. | 2.827 | 14302 | 8.1 |
| 31.88 | 2.805 | 8467 | 4.8 |

TABLE 6-continued

XRPD peak list of Form ζ

| 2θ | d spacing, A° | Count | % |
|---|---|---|---|
| 32.39 | 2.762 | 12007 | 6.8 |
| 33.42 | 2.679 | 3102 | 1.8 |
| 33.93 | 2.640 | 28295 | 16 |
| 34.59 | 2.591 | 5340 | 3 |
| 35.08 | 2.556 | 10972 | 6.2 |
| 36.49 | 2.460 | 11523 | 6.5 |
| 36.92 | 2.433 | 7022 | 4 |
| 37.62 | 2.389 | 4998 | 2.8 |
| 38.25 | 2.351 | 3796 | 2.1 |
| 38.89 | 2.311 | 5009 | 2.8 |
| 39.24 | 2.294 | 5205 | 2.9 |
| 39.80 | 2.263 | 6548 | 3.7 |

Figure 8:
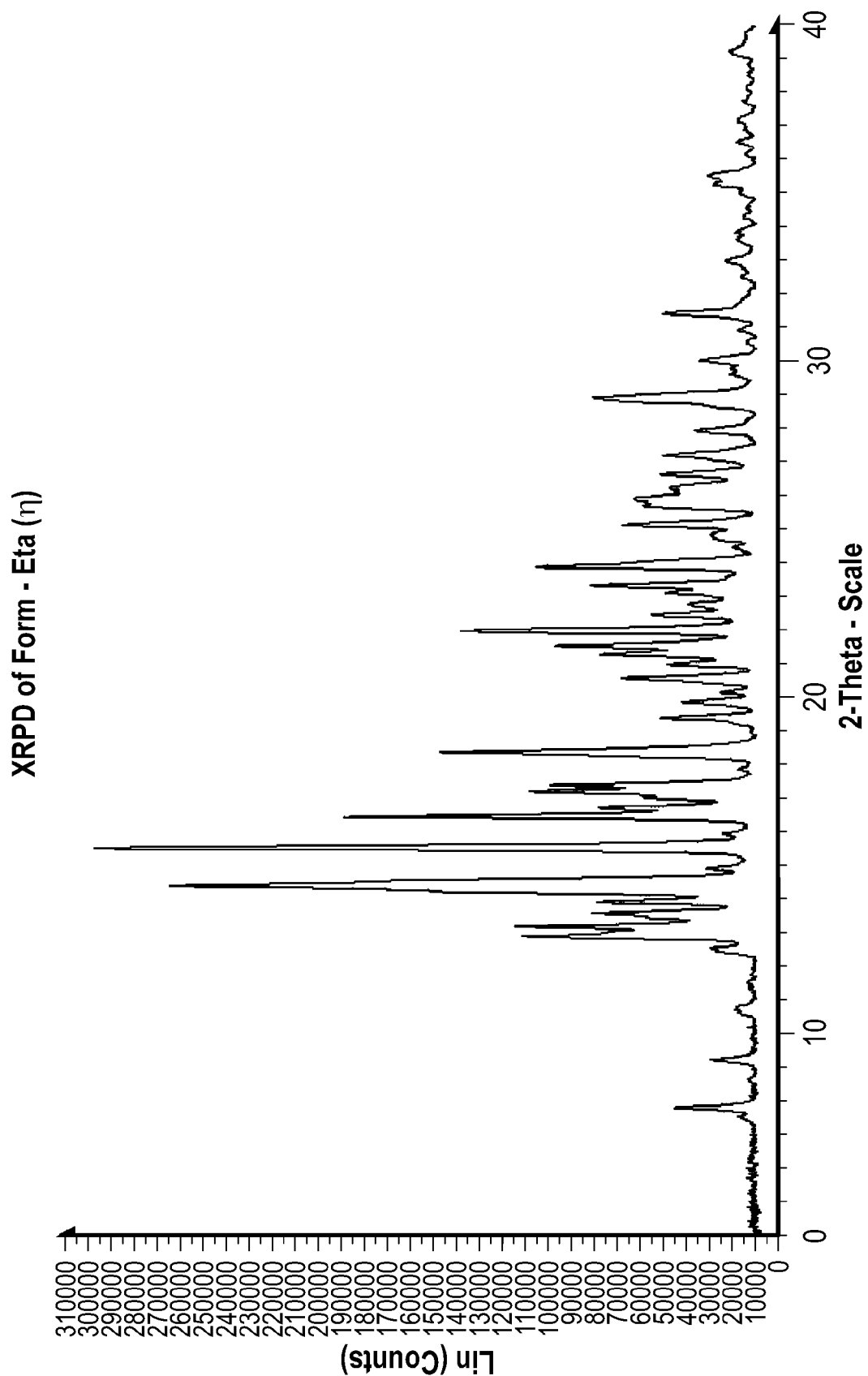
FIG. 8 is an X-ray powder diffractogram of morphine sulfate crystalline Form $\eta$, expressed in terms of °2θ.

Morphine sulfate Form η is a unique crystalline phase. Morphine sulfate Form η may be characterized as a white to off-white powder. Morphine sulfate Form η is further characterized by its X-ray powder diffraction pattern peaks and/or d-spacing values, as listed in Table 7 below. FIG. 8 is a representative X-ray powder diffractogram for a representative sample of morphine sulfate Form η made according to Example 10.

TABLE 7

XRPD peak list of Form η

| 2θ | d spacing, A° | Count | % |
|---|---|---|---|
| 7.75 | 11.405 | 4463 | 15 |
| 9.16 | 9.643 | 2920 | 9.8 |
| 10.71 | 8.258 | 1812 | 6.1 |
| 12.46 | 7.100 | 2817 | 9.5 |
| 12.87 | 6.875 | 11111 | 37.3 |
| 13.15 | 6.727 | 11390 | 38.3 |
| 13.52 | 6.545 | 8090 | 27.2 |
| 13.88 | 6.374 | 7809 | 26.2 |
| 14.36 | 6.162 | 26492 | 89 |
| 14.87 | 5.952 | 3086 | 10.4 |
| 15.49 | 5.717 | 29771 | 100 |
| 16.42 | 5.394 | 18857 | 63.3 |
| 16.68 | 5.311 | 7777 | 26.1 |
| 17.19 | 5.156 | 10816 | 36.3 |
| 17.36 | 5.103 | 9882 | 33.2 |
| 18.33 | 4.835 | 14720 | 49.4 |
| 19.37 | 4.580 | 5087 | 17.1 |
| 19.83 | 4.473 | 4094 | 13.8 |
| 20.14 | 4.405 | 2502 | 8.4 |
| 20.54 | 4.320 | 6772 | 22.7 |
| 20.97 | 4.234 | 4808 | 16.2 |
| 21.27 | 4.175 | 7703 | 25.9 |
| 21.51 | 4.128 | 9621 | 32.3 |
| 21.96 | 4.045 | 13770 | 46.3 |
| 22.44 | 3.959 | 5453 | 18.3 |
| 22.73 | 3.909 | 3857 | 13 |
| 23.09 | 3.848 | 4832 | 16.2 |
| 23.31 | 3.813 | 8138 | 27.3 |
| 23.88 | 3.723 | 10490 | 35.2 |
| 24.81 | 3.585 | 2936 | 9.9 |
| 25.12 | 3.542 | 6737 | 22.6 |
| 25.70 | 3.463 | 5827 | 19.6 |
| 25.88 | 3.440 | 6250 | 21 |
| 26.21 | 3.397 | 4614 | 15.5 |
| 26.64 | 3.344 | 5066 | 17 |
| 27.20 | 3.276 | 4950 | 16.6 |
| 27.93 | 3.192 | 3596 | 12.1 |
| 28.89 | 3.088 | 7990 | 26.8 |
| 30.03 | 2.974 | 3414 | 11.5 |
| 31.43 | 2.844 | 4953 | 16.6 |
| 32.98 | 2.713 | 2238 | 7.5 |
| 35.52 | 2.525 | 3025 | 10.2 |
| 39.21 | 2.296 | 2068 | 6.9 |

Figure 9:
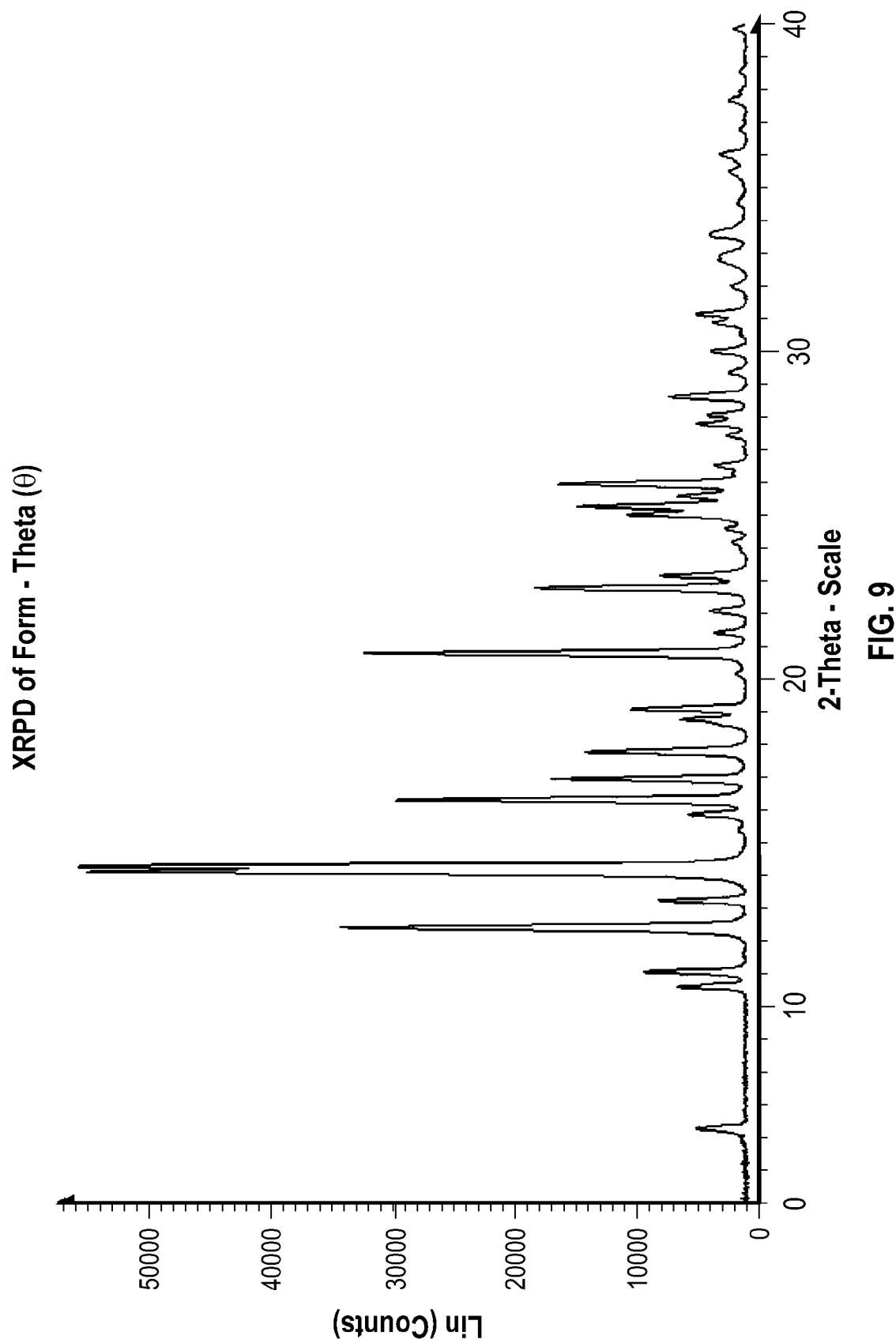
FIG. 9 is an X-ray powder diffractogram of morphine sulfate crystalline Form $\theta$, expressed in terms of °2θ.
Figure 10:
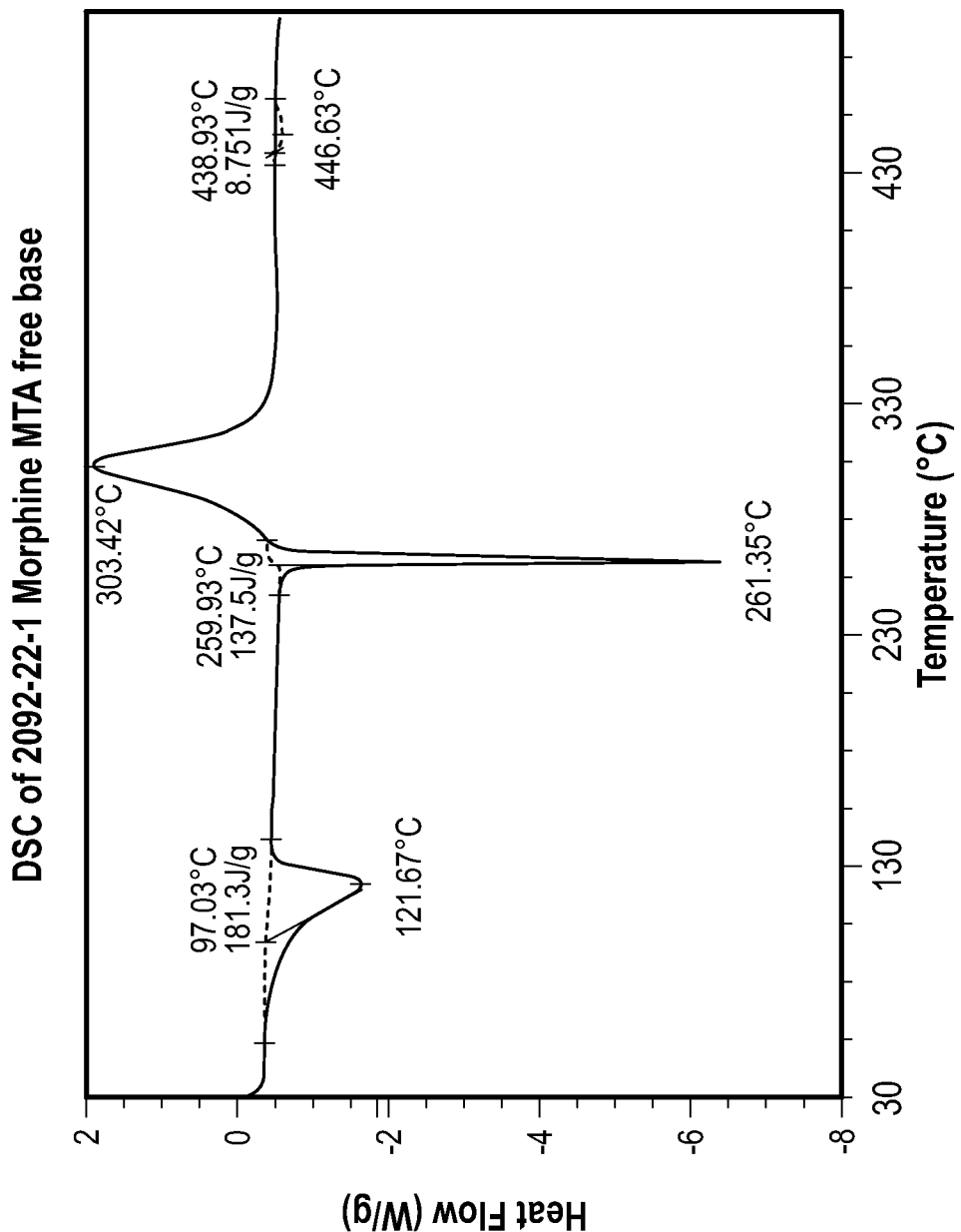
FIG. 10 is a measured differential scanning calorimetry thermogram of morphine free base.

Morphine sulfate Form θ is a unique crystalline phase. Morphine sulfate Form θ may be characterized as a white to off-white powder. Morphine sulfate Form θ is further characterized by its X-ray powder diffraction pattern peaks and/or d-spacing values, as listed in Table 8 below. FIG. 9 is a representative X-ray powder diffractogram for a representative sample of morphine sulfate Form θ made according to Example 11.

TABLE 8

XRPD peak list of Form θ

| 2θ | d spacing, A° | Count | % |
|---|---|---|---|
| 4.17 | 4.172 | 44.5 | 0.1 |
| 4.27 | 4.269 | 36.4 | 0.1 |
| 6.20 | 6.197 | 4012 | 7.3 |
| 10.56 | 10.556 | 5607 | 10.2 |
| 11.00 | 11.001 | 8375 | 15.3 |
| 12.36 | 12.359 | 33350 | 60.8 |
| 13.18 | 13.180 | 7125 | 13 |
| 14.05 | 14.050 | 54408 | 99.2 |
| 14.22 | 14.215 | 54834 | 100 |
| 15.33 | 15.328 | 599 | 1.1 |
| 15.81 | 15.812 | 4672 | 8.5 |
| 16.26 | 16.255 | 28665 | 52.3 |
| 16.90 | 16.897 | 15956 | 29.1 |
| 17.73 | 17.726 | 13145 | 24 |
| 18.72. | 18.716 | 5306 | 9.7 |
| 19.03 | 19.026 | 9348 | 17 |
| 20.12 | 20.118 | 828 | 1.5 |
| 20.73 | 20.733 | 31446 | 57.3 |
| 21.38 | 21.376 | 2555 | 4.7 |
| 22.04 | 22.037 | 2930 | 5.3 |
| 22.74 | 22.742 | 17287 | 31.5 |
| 23.11 | 23.109 | 6983 | 12.7 |
| 24.14 | 24.138 | 1040 | 1.9 |
| 24.54 | 24.538 | 1670 | 3 |
| 24.99 | 24.990 | 9728 | 17.7 |
| 25.25 | 25.247 | 13894 | 25.3 |
| 25.56 | 25.561 | 5572 | 10.2 |
| 25.92 | 25.923 | 15440 | 28.2 |
| 26.50 | 26.496 | 2590 | 4.7 |
| 27.40 | 27.402 | 1552 | 2.8 |
| 27.75 | 27.752 | 4031 | 7.4 |
| 28.03 | 28.025 | 3130 | 5.7 |
| 28.59 | 28.592 | 6237 | 11.4 |
| 29.34 | 29.335 | 1363 | 2.5 |
| 29.98 | 29.979 | 2835 | 5.2 |
| 30.85 | 30.848 | 2642 | 4.8 |
| 31.12 | 31.121 | 4001 | 7.3 |
| 31.96 | 31.961 | 1156 | 2.1 |
| 32.82 | 32.815 | 2220 | 4 |
| 33.55 | 33.549 | 2879 | 5.3 |
| 34.52 | 34.515 | 634 | 1.2 |
| 35.48 | 35.477 | 1388 | 2.5 |
| 36.01 | 36.005 | 2078 | 3.8 |
| 36.75 | 36.752 | 441 | 0.8 |
| 37.65 | 37.653 | 1361 | 2.5 |
| 38.53 | 38.534 | 475 | 0.9 |
| 39.84 | 39.838 | 946 | 1.7 |

Differential scanning calorimetry is performed using a TA Instruments Q10 DSC. Typically, samples are placed in unsealed, covered hermetic alodined aluminum sample pans and scanned from about 30° C. to about 300° C. at a rate of about 10° C./min under a nitrogen purge of about 50 mL/min.

Differential scanning calorimetry is performed on representative samples of morphine sulfate Forms α, β, γ, δ, ε, ζ, η and θ, as shown in FIGS. 11, 12, 13, 14, 15, 16, 17 and 18, respectively. Two thermal events may be observed in the differential scanning calorimetry thermogram for morphine sulfate Form α at about 117° C. and about 173° C. Two thermal events may be observed in the differential scanning calorimetry thermogram for morphine sulfate Form β at about 112° C. and about 177° C. Two thermal events may be observed in the differential scanning calorimetry thermogram for morphine sulfate Form γ at about 140° C. and about 234° C. Three thermal events may be observed in the differential scanning calorimetry thermogram for morphine sulfate Form δ at about 58° C., 136° C. and about 221° C. One thermal event may be observed in the differential scanning calorimetry thermogram for morphine sulfate Form ε at about 160° C. Two thermal events may be observed in the differential scanning calorimetry thermogram for morphine sulfate Form ζ at about 163° C. and about 238° C. One thermal event may be observed in the differential scanning calorimetry thermogram for morphine sulfate Form η at about 284° C. Two thermal events may be observed in the differential scanning calorimetry thermogram for morphine sulfate Form θ at about 158° C. and about 237° C.

The present disclosure also describes pharmaceutical compositions comprising one or more of the morphine sulfate crystalline forms as herein described in association with conventional excipients, i.e., pharmaceutically acceptable organic or inorganic carrier substances. These compositions may be in dosage forms such as, but not limited to, tablets, pills, capsules, powders, granules, sterile parenteral solutions or suspensions, metered aerosol or liquid sprays, drops, ampoules, autoinjector devices or suppositories; for oral, parenteral, intranasal, sublingual or rectal administration, or for administration by inhalation or insufflation.

To prepare a pharmaceutical composition of the present disclosure, any one or more of the morphine sulfate crystalline forms as herein described is intimately admixed with a pharmaceutical excipient according to conventional pharmaceutical compounding techniques, which excipient may take a wide variety of forms depending of the form of preparation desired for administration (e.g. oral or parenteral). Suitable pharmaceutically acceptable excipients include those known in the art and those yet to be discovered. Descriptions of some of these pharmaceutically acceptable excipients may be found in *The Handbook of Pharmaceutical Excipients* and the Pharmaceutical Society of Great Britain. The pharmaceutical compositions of the present disclosure may be prepared according to any method known in the art as well as yet to be discovered improvements thereto. Methods of formulating pharmaceutical compositions have been described in numerous publications such as *Pharmaceutical Dosage Forms: Tablets, Second Edition, Revised and Expanded*, Volumes 1-3; *Pharmaceutical Dosage Forms: Parenteral Medications*, Volumes 1-2; and *Pharmaceutical Dosage Forms: Disperse Systems*, Volumes 1-2.

The oral formulations of the present disclosure may be coated or otherwise compounded to provide a dosage form affording the advantage of prolonged action. The sustained release dosage forms may optionally comprise particles containing any one or more of the morphine sulfate forms as herein described. Preferably, the particles are film coated with a material that permits release of the active at a sustained rate in an aqueous medium. The film coat is chosen so as to achieve, in combination with the other stated properties, desired release properties. The sustained release coating formulations of the present disclosure should preferably be capable of producing a strong, continuous film that is smooth and elegant, capable of supporting pigments and other coating additives, non-toxic, inert and tack-free. The sustained release formulations of the present disclosure preferably slowly release the active agent(s), e.g., when ingested and exposed to gastric fluids, and then to intestinal fluids. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate. Sustained release dosage forms according to the present disclosure may also be prepared as osmotic dosage formulations known in the art as well as improvements thereto.

The liquid forms in which the novel compositions of the present disclosure may be incorporated for administration orally or by injectable include, aqueous solutions, suitably flavored syrups, aqueous or oil suspensions, and flavored emulsions with edible oils as well as elixirs and similar pharmaceutical vehicles. The liquid forms may include suitably flavored suspending or dispersing agents such as the synthetic and natural gums. For parenteral administration, sterile suspensions and solutions are desired. Isotonic preparations which generally contain suitable preservative are employed when intravenous administration is desired.

The formulations of the present disclosure may be formulated as a pharmaceutical suppository for rectal administration comprising a suitable suppository base, and any one or more of the morphine sulfate crystalline forms as herein described. This includes the preparation of sustained release suppository formulations as described in U.S. Pat. No. 5,215,758.

The compounds of the present disclosure may be administered in intranasal form via topical use of suitable intranasal vehicles, or via transdermal skin patches well known to those of ordinary skill in the art. To be administered in the form of a transdermal delivery system, the dosage administration will be continuous rather than intermittent throughout the dosage regimen.

The present disclosure provides for a method of treating pain by administering to a subject in need thereof the dosage forms described above which contain any one or more of the morphine sulfate crystalline forms as herein described. The dosage of the products may be varied over a wide range. Optimal dosages and dosage regimens to be administered may be readily determined by those skilled in the art, and will vary with the mode of administration, the strength of the preparation and the advancement of the disease condition. In addition, factors associated with the particular subject being treated, including subject's sex, age, weight, diet, physical activity, time of administration and concomitant diseases, will result in the need to adjust dosages and/or regimens.

EXAMPLES

The disclosure is illustrated by the following examples.

The following examples are set forth to aid in the understanding of the disclosure, and are not intended and should not be construed to limit in any way the disclosure set forth in the claims which follow thereafter. Although illustrated and herein described with reference to certain specific embodiments, the present disclosure is nevertheless not intended to be limited to the details shown. Rather, various modifications may be made in the details within the scope and range of equivalents of the claims and without departing from the spirit of the disclosure.

Example 1

Preparation of Morphine Sulfate

Morphine Technical Alkaloid (MTA) material is combined with water and 0.5 equiv. of 50% isopropyl acetate diluted sulfuric acid. The mixture is heated to about 75° C. and cooled to about 15° C. at a rate of about 0.23° C. per minute. The resulting mixture is filtered under vacuum and washed with ethanol. The filtrate is dried at about 50° C. under vacuum. The resulting solids are determined to be morphine sulfate.

Example 2

Preparation of Morphine Free Base

About 8.43 g of morphine sulfate and about 40 mL of water are added to an Easy Max™ set at 350 RPM agitation rate. The mixture becomes clear and is then heated to about 65° C. The pH is checked and determined to be about 5. About 10 mL of pre-made solution in water of 1 M NaOH is added to the mixture. Solids are formed. About 5 mL of pre-made solution in water of 1 M NaOH is added to the mixture. The pH is checked and determined to be about 6. A few NaOH pellets are added to the mixture. Heating and stirring is continued for about 2 hours. The mixture is then cooled to about 50° C., filtered under vacuum filtration and washed several times with water. The pH of the filtrate is checked and determined to be about 13. The filtrate is dried at about 45° C. under vacuum for about 12-24 hours. The resulting solids are analyzed by X-ray powder diffraction and determined to be morphine free base.

Example 3

Preparation of Form α Using Acetone

About 200 mg of morphine free base and about 1 mL of acetone are added to a vial. Concentrated sulfuric acid is pre-diluted in isopropanol. About 49 μL of 50% isopropyl acetate diluted sulfuric acid is added to the vial. The mixture is stirred for about 4 to 5 hours at about 20 to 26° C. The resulting slurry is analyzed by X-ray powder diffraction and determined to be morphine sulfate Form α.

Example 4

Preparation of Form α Using Water

About 200 mg of morphine free base and about 1 mL of water are added to a vial. Concentrated sulfuric acid is pre-diluted in isopropanol. About 49 μL of 50% isopropyl acetate diluted sulfuric acid is added to the vial. The mixture is stirred for about 4 to 5 hours at about 55 to 65° C. The resulting solids are analyzed by X-ray powder diffraction and determined to be morphine sulfate Form α.

Example 5

Preparation of Form β Using Isopropyl Acetate

About 200 mg of morphine free base and about 1 mL of isopropyl acetate are added to a vial. Concentrated sulfuric acid is pre-diluted in isopropanol. About 49 μL of 50% isopropyl acetate diluted sulfuric acid is added to the vial. The mixture is stirred for about 4 to 5 hours at about 20 to 26° C. The resulting solids are analyzed by X-ray powder diffraction and determined to be morphine sulfate Form β.

Example 6

Preparation of Form γ Using Acetone

About 200 mg of morphine free base and about 1 mL of acetone are added to a vial. Concentrated sulfuric acid is pre-diluted in isopropanol. About 49 μL of 50% isopropyl acetate diluted sulfuric acid is added to the vial. The mixture is stirred for about 4 to 5 hours at about 55 to 65° C. The resulting solids are analyzed by X-ray powder diffraction and determined to be morphine sulfate Form γ.

Example 7

Preparation of Form δ Using Ethanol

About 200 mg of morphine free base and about 1 mL of ethanol are added to a vial. Concentrated sulfuric acid is pre-diluted in isopropanol. About 49 μL of 50% isopropyl acetate diluted sulfuric acid is added to the vial. The mixture is stirred for about 4 to 5 hours at about 20 to 26° C. The resulting solids are analyzed by X-ray powder diffraction and determined to be morphine sulfate Form δ.

Example 8

Preparation of Form ε Using Methanol

About 200 mg of morphine free base and about 1 mL of methanol are added to a vial. Concentrated sulfuric acid is pre-diluted in isopropanol. About 49 μL of 50% isopropyl acetate diluted sulfuric acid is added to the vial. The mixture is stirred for about 4 to 5 hours at about 20 to 26° C. The resulting solids are analyzed by X-ray powder diffraction and determined to be morphine sulfate Form ε.

Example 9

Preparation of Form ζ Using Water

About 200 mg of morphine free base and about 1 mL of water are added to a vial. Concentrated sulfuric acid is pre-diluted in isopropanol. About 49 μL of 50% isopropyl acetate diluted sulfuric acid is added to the vial. The mixture is stirred for about 4 to 5 hours at about 20 to 26° C. The resulting solids are analyzed by X-ray powder diffraction and determined to be morphine sulfate Form ζ.

Example 10

Preparation of Form η Using Ethanol/Methanol

About 200 mg of morphine free base and about 1 mL of ethanol/methanol 80:20 are added to a vial. Concentrated sulfuric acid is pre-diluted in isopropanol. About 49 μL of 50% isopropyl acetate diluted sulfuric acid is added to the vial. The mixture is stirred for about 4 to 5 hours at about 20 to 26° C. The resulting solids are analyzed by X-ray powder diffraction and determined to be morphine sulfate Form η.

Example 11

Preparation of Form θ Using Water

About 5 mg of MTA material, about 11 mL of water and a 50% solution of about 0.7 sulfuric acid equiv. are heated to about 70° C. The mixture is cooled at a rate of about 1.05° C. per minute with fast agitation (about 800 RPM) over about 2.5 hours. The resulting solids are analyzed by X-ray powder diffraction and determined to be morphine sulfate Form θ.

What is claimed is:

1. A form of morphine sulfate selected from the group consisting of Form α, Form β, Form γ, Form δ, Form ε, Form ζ, Form η and Form θ; wherein:
Form α has an X-ray powder diffraction pattern comprising peaks, in terms of 2-theta, at about 15.71 and about 17.08;
Form β has an X-ray powder diffraction pattern comprising peaks, in terms of 2-theta, at about 15.43 and about 17.78;
Form γ has an X-ray powder diffraction pattern comprising peaks, in terms of 2-theta, at about 14.28 and about 13.21;
Form δ has an X-ray powder diffraction pattern comprising peaks, in terms of 2-theta, at about 15.68 and about 17.03;
Form ε has an X-ray powder diffraction pattern comprising peaks, in terms of 2-theta, at about 14.40 and about 23.58;
Form ζ has an X-ray powder diffraction pattern comprising peaks, in terms of 2-theta, at about 14.28 and about 20.44;
Form η has an X-ray powder diffraction pattern comprising peaks, in terms of 2-theta, at about 15.49 and about 14.36; and
Form θ has an X-ray powder diffraction pattern comprising peaks, in terms of 2-theta, at about 14.22 and about 14.05.

2. A form of morphine sulfate according to claim 1, wherein:
Form α has an X-ray powder diffraction pattern further comprising peaks, in terms of 2-theta, at about 17.63, about 13.45 and about 15.48;
Form β has an X-ray powder diffraction pattern further comprising peaks, in terms of 2-theta, at about 13.68, about 16.89 and about 20.58;
Form γ has an X-ray powder diffraction pattern further comprising peaks, in terms of 2-theta, at about 16.95, about 17.47 and about 15.63;
Form δ has an X-ray powder diffraction pattern further comprising peaks, in terms of 2-theta, at about 17.54, about 20.64 and about 26.20;
Form ε has an X-ray powder diffraction pattern further comprising peaks, in terms of 2-theta, at about 10.80, about 19.20 and about 13.54;
Form ζ has an X-ray powder diffraction pattern further comprising peaks, in terms of 2-theta, at about 13.67, about 24.24 and about 26.39;
Form η has an X-ray powder diffraction pattern further comprising peaks, in terms of 2-theta, at about 16.42, about 18.33 and about 21.96; and
Form θ has an X-ray powder diffraction pattern further comprising a peak, in terms of 2-theta, at about 12.36, about 20.73 and about 16.26.

3. A form of morphine sulfate selected from the group consisting of Form α, Form β, Form γ, Form δ, Form ε, Form ζ, Form η and Form θ; wherein:
Form α has an X-ray powder diffraction pattern substantially as shown in FIG. 2;
Form β has an X-ray powder diffraction pattern substantially as shown in FIG. 3;
Form γ has an X-ray powder diffraction pattern substantially as shown in FIG. 4;
Form δ has an X-ray powder diffraction pattern substantially as shown in FIG. 5;
Form ε has an X-ray powder diffraction pattern substantially as shown in FIG. 6;
Form ζ has an X-ray powder diffraction pattern substantially as shown in FIG. 7;
Form η has an X-ray powder diffraction pattern substantially as shown in FIG. 8; and
Form θ has an X-ray powder diffraction pattern substantially as shown in FIG. 9.

4. A form of morphine sulfate selected from the group consisting of Form α, Form β, Form γ, Form δ, Form ε, Form ζ, Form η and Form θ according to claim 1; wherein:
Form α has an X-ray powder diffraction pattern comprising peaks at d-spacing, in terms of Angstroms, of about 5.635 and about 5.187;
Form β has an X-ray powder diffraction pattern comprising peaks at d-spacing, in terms of Angstroms, of about 5.738 and about 4.984;
Form γ has an X-ray powder diffraction pattern comprising peaks at d-spacing, in terms of Angstroms, of about 6.195 and about 6.695;
Form δ has an X-ray powder diffraction pattern comprising peaks at d-spacing, in terms of Angstroms, of about 5.646 and about 5.203;
Form ε has an X-ray powder diffraction pattern comprising peaks at d-spacing, in terms of Angstroms, of about 6.145 and about 3.770;
Form ζ has an X-ray powder diffraction pattern comprising peaks at d-spacing, in terms of Angstroms, of about 6.198 and about 4.342;
Form η has an X-ray powder diffraction pattern comprising peaks at d-spacing, in terms of Angstroms, of about 5.717 and about 6.162; and
Form θ has an X-ray powder diffraction pattern comprising peaks at d-spacing, in terms of Angstroms, of about 14.215 and about 14.050.

5. A form of morphine sulfate according to claim 4, wherein:
Form α has an X-ray powder diffraction pattern further comprising peaks at d-spacing, in terms of Angstroms, of about 5.026, about 6.576 and about 5.721;
Form β has an X-ray powder diffraction pattern further comprising peaks at d-spacing, in terms of Angstroms, of about 6.468, about 5.246 and about 4.313;
Form γ has an X-ray powder diffraction pattern further comprising peaks at d-spacing, in terms of Angstroms, of about 5.227, about 5.073 and about 5.666;
Form δ has an X-ray powder diffraction pattern further comprising peaks at d-spacing, in terms of Angstroms, of about 5.051, about 4.299 and about 3.398;
Form ε has an X-ray powder diffraction further comprising peaks at d-spacing, in terms of Angstroms, of about 8.189, about 4.620 and about 6.535;
Form ζ has an X-ray powder diffraction pattern further comprising peaks at d-spacing, in terms of Angstroms, of about 6.475, about 3.668 and about 3.374;
Form η has an X-ray powder diffraction pattern further comprising peaks at d-spacing, in terms of Angstroms, of about 5.394, about 4.835 and about 4.045; and
Form θ has an X-ray powder diffraction further comprising peaks at d-spacing, in terms of Angstroms, of about 12.359, about 20.733 and about 16.255.

6. A form of morphine sulfate according to claim 1, wherein, as measured by differential scanning calorimetry:
Form α is characterized by an endotherm at about 173° C.;
Form β is characterized by an endotherm at about 177° C.;
Form γ is characterized by an endotherm at about 234° C.;
Form δ is characterized by an endotherm at about 58° C.;
Form ε is characterized by an endotherm at about 160° C.;
Form ζ is characterized by an endotherm at about 163° C.;

Form η is characterized by an endotherm at about 284° C.; and

Form θ is characterized by an endotherm at about 158° C.

Figure 11:
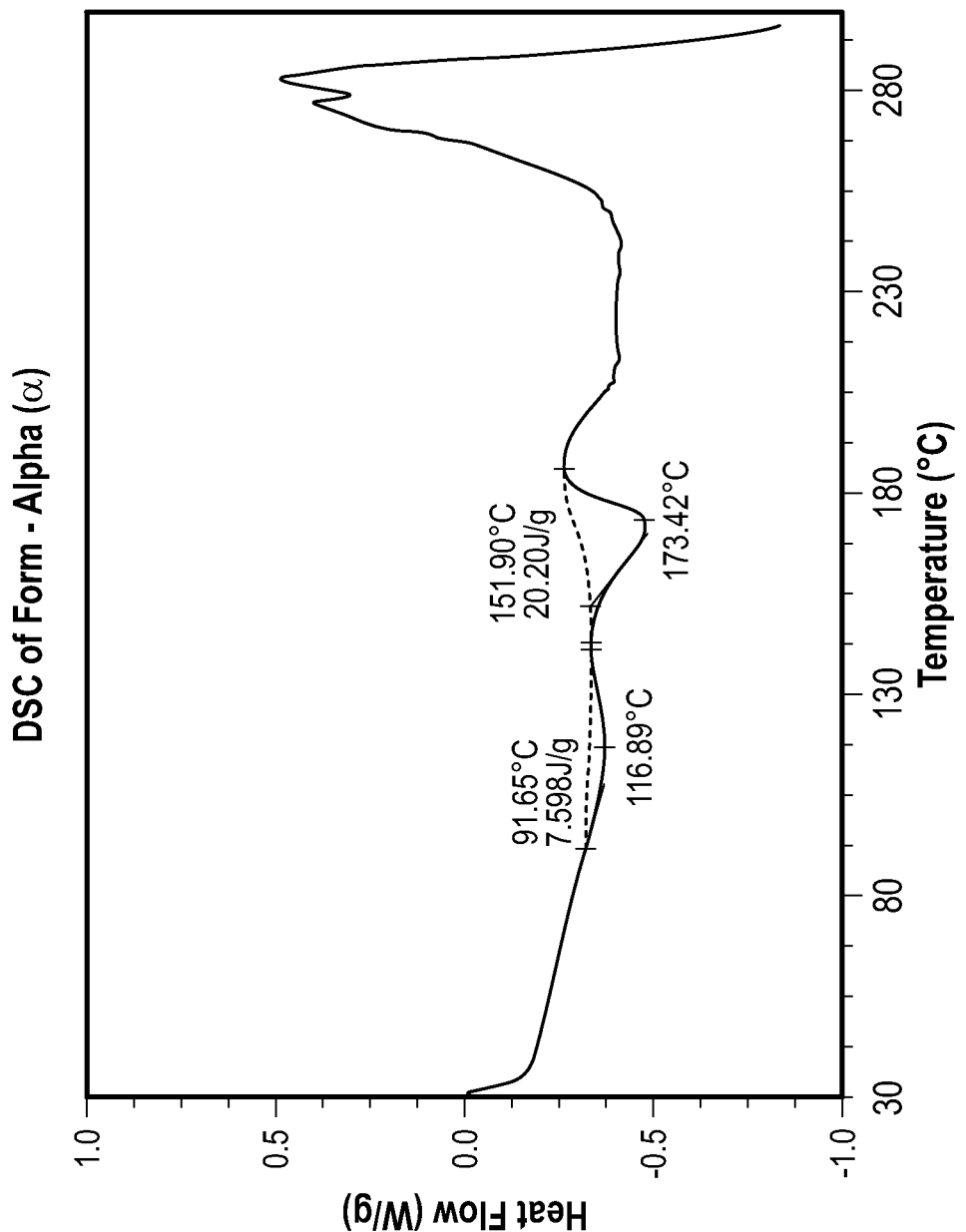
FIG. 11 is a measured differential scanning calorimetry thermogram of morphine sulfate crystalline Form $\alpha$.
Figure 12:
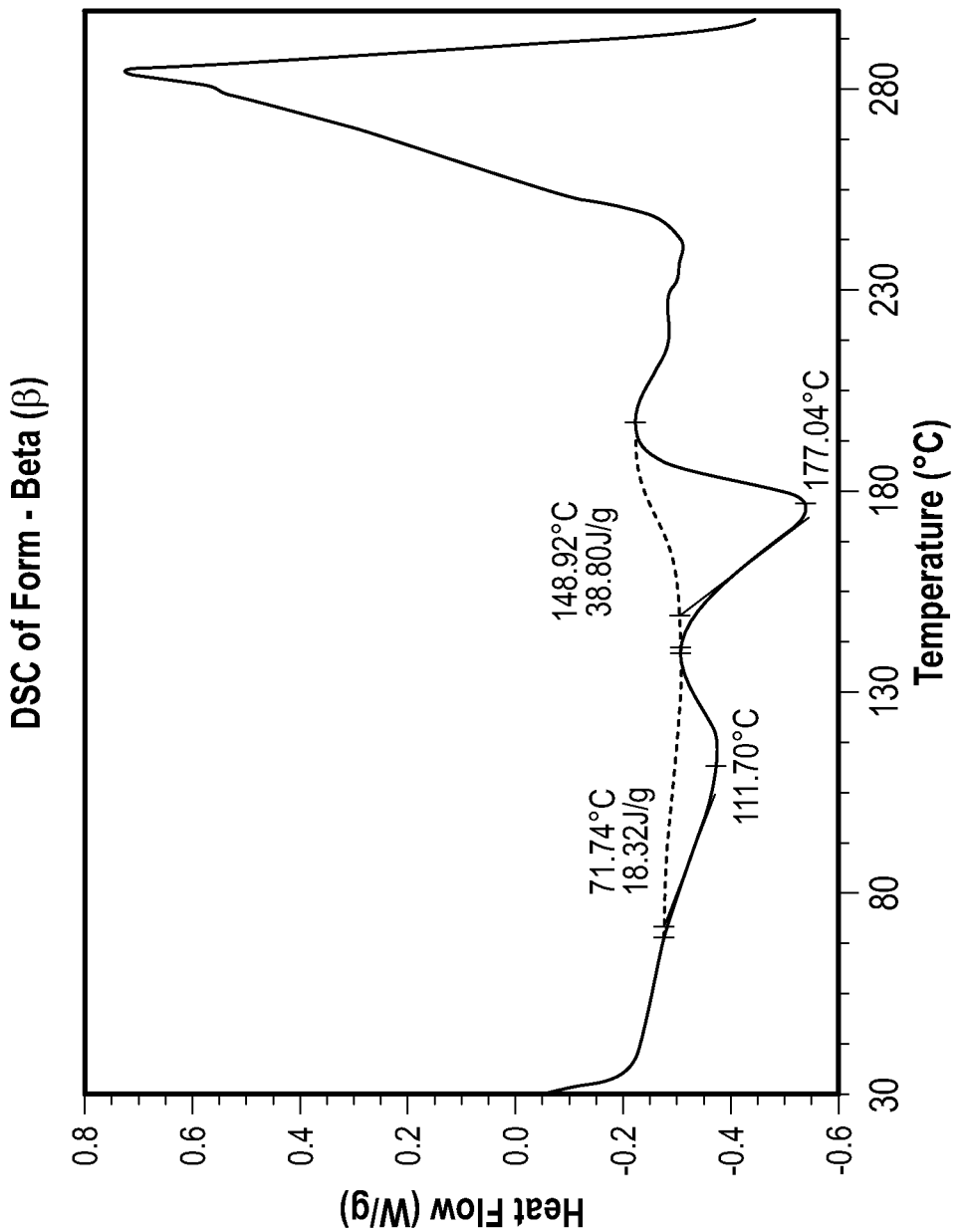
FIG. 12 is a measured differential scanning calorimetry thermogram of morphine sulfate crystalline Form $\beta$.
Figure 13:
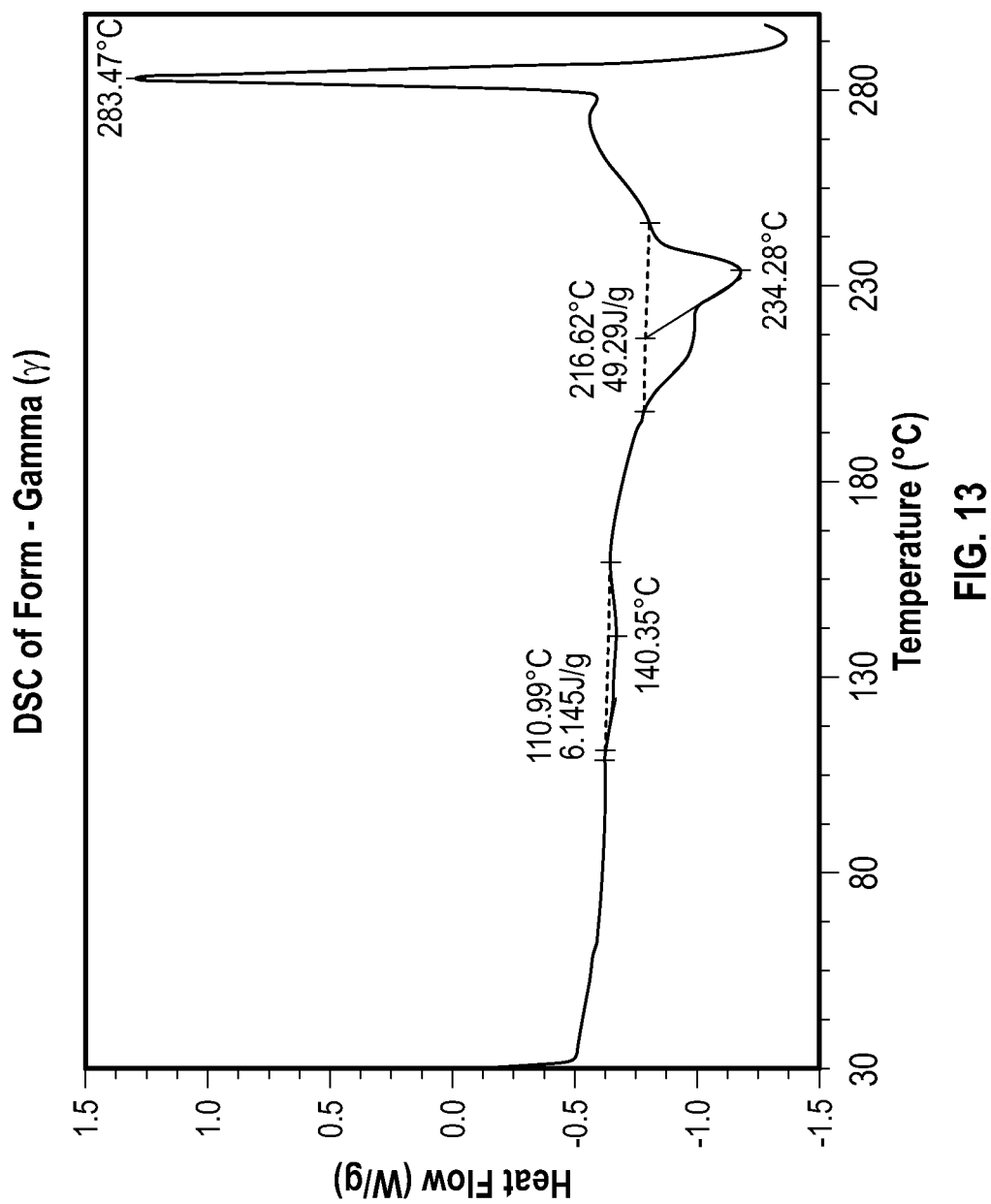
FIG. 13 is a measured differential scanning calorimetry thermogram of morphine sulfate crystalline Form $\gamma$.
Figure 14:
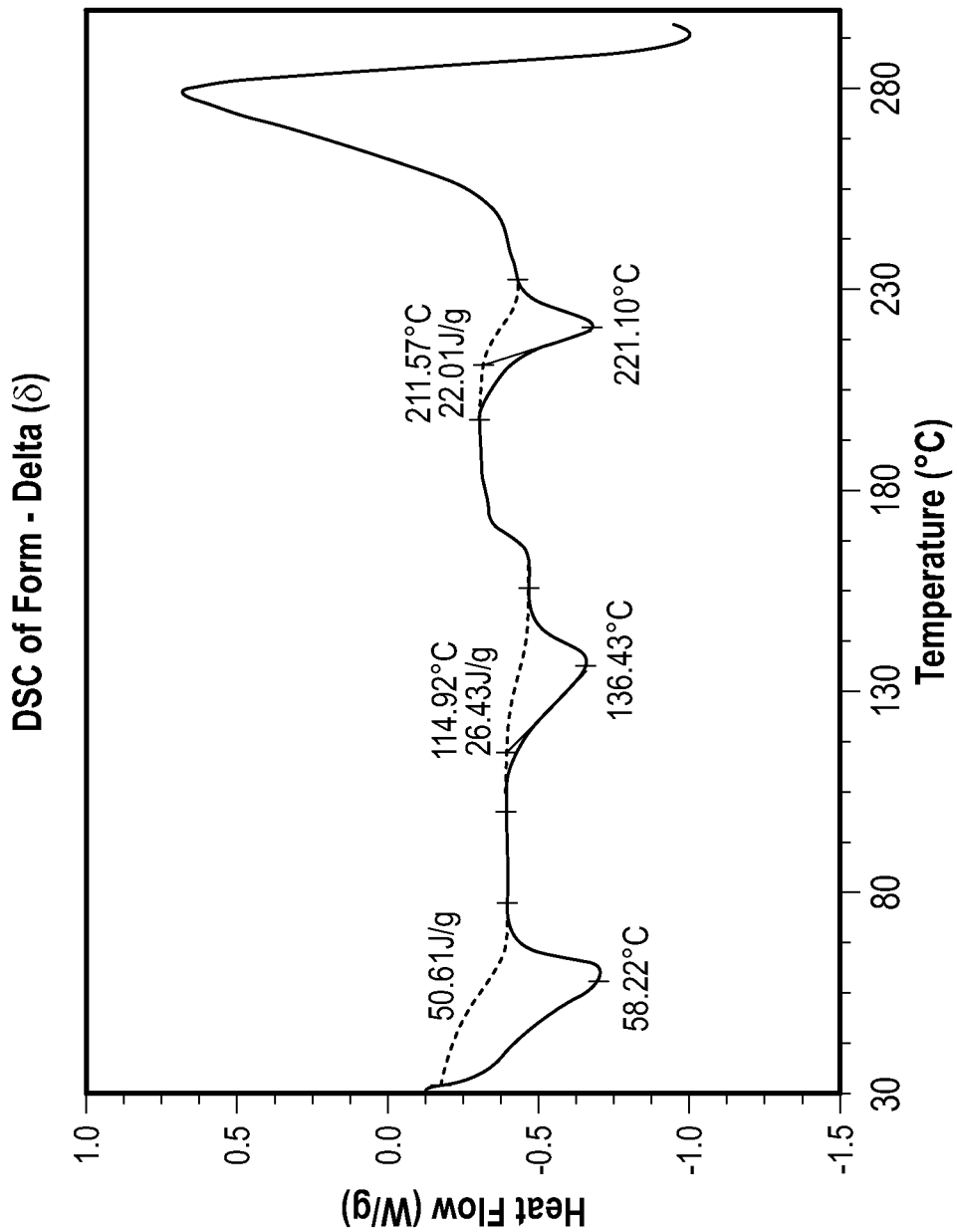
FIG. 14 is a measured differential scanning calorimetry thermogram of morphine sulfate crystalline Form $\delta$.
Figure 15:
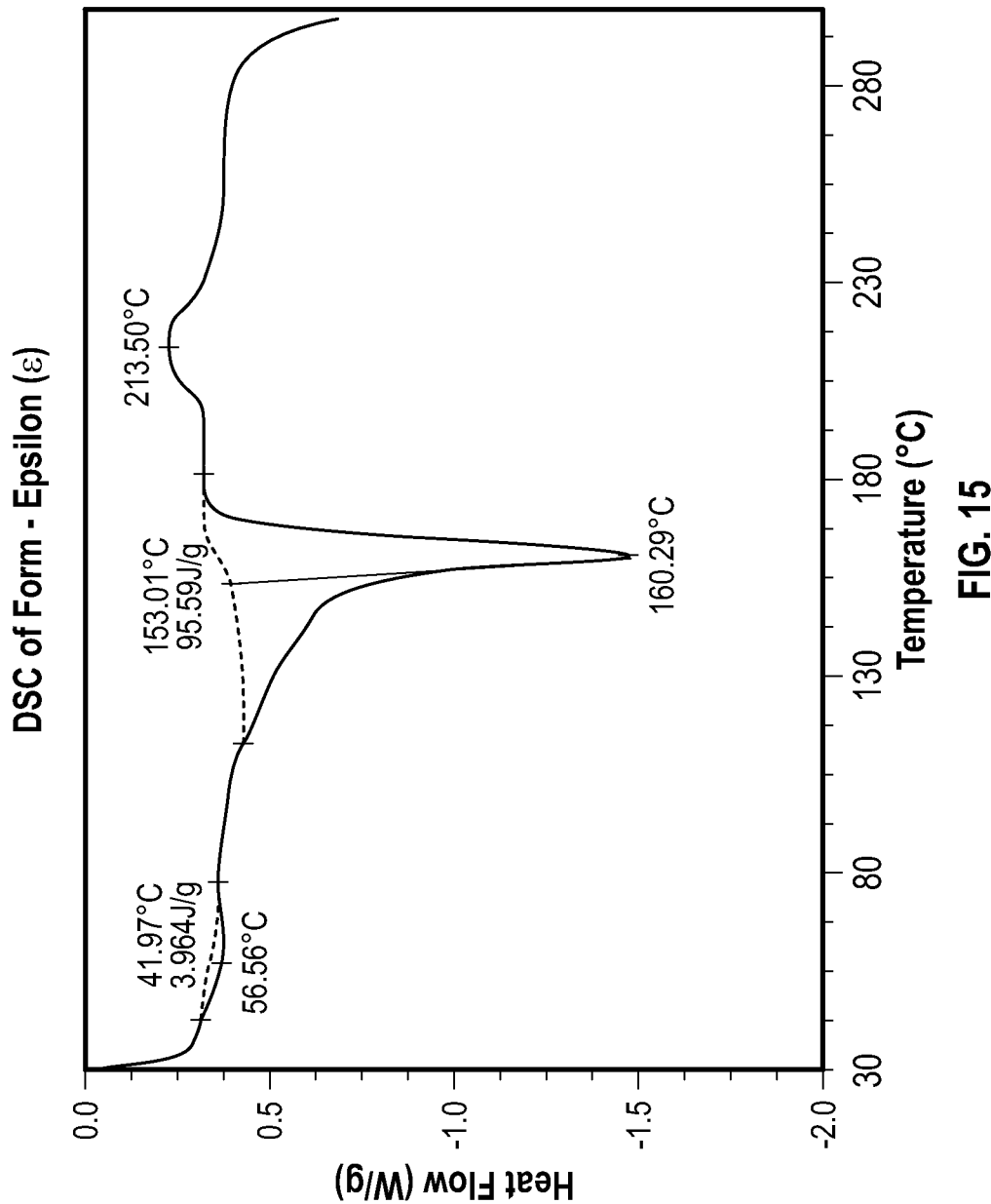
FIG. 15 is a measured differential scanning calorimetry thermogram of morphine sulfate crystalline Form $\epsilon$.
Figure 16:
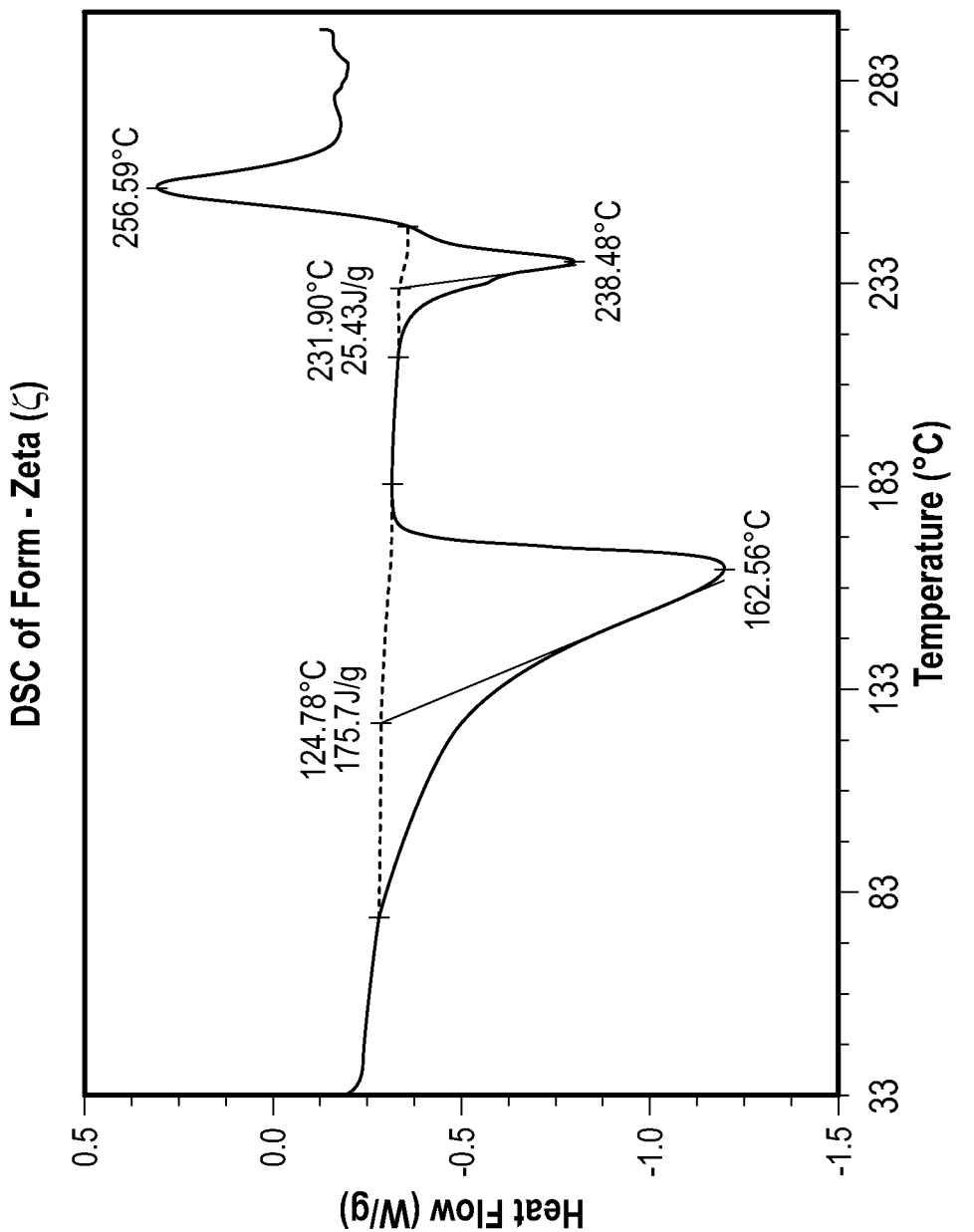
FIG. 16 is a measured differential scanning calorimetry thermogram of morphine sulfate crystalline Form $\zeta$.
Figure 17:
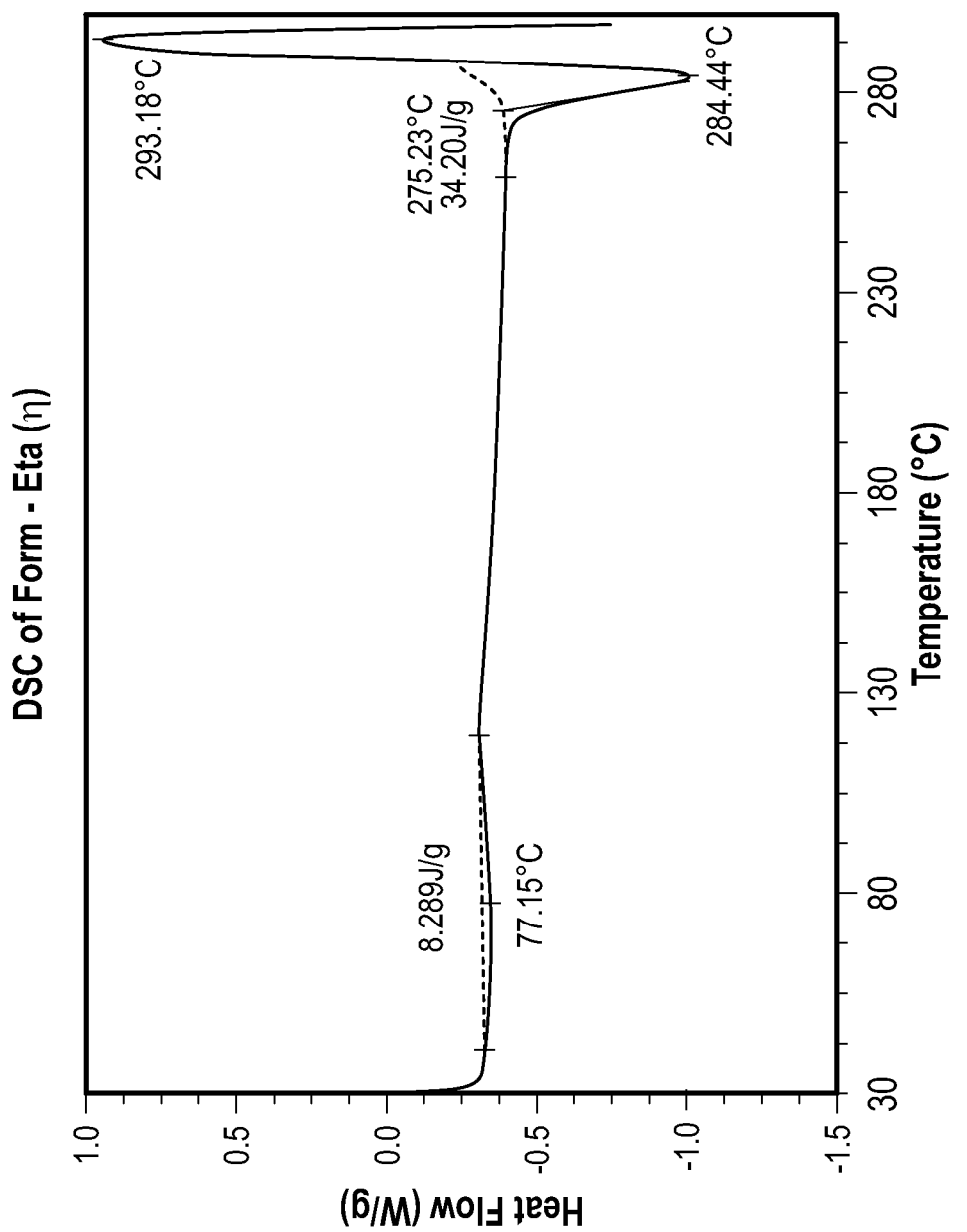
FIG. 17 is a measured differential scanning calorimetry thermogram of morphine sulfate crystalline Form $\eta$.
Figure 18:
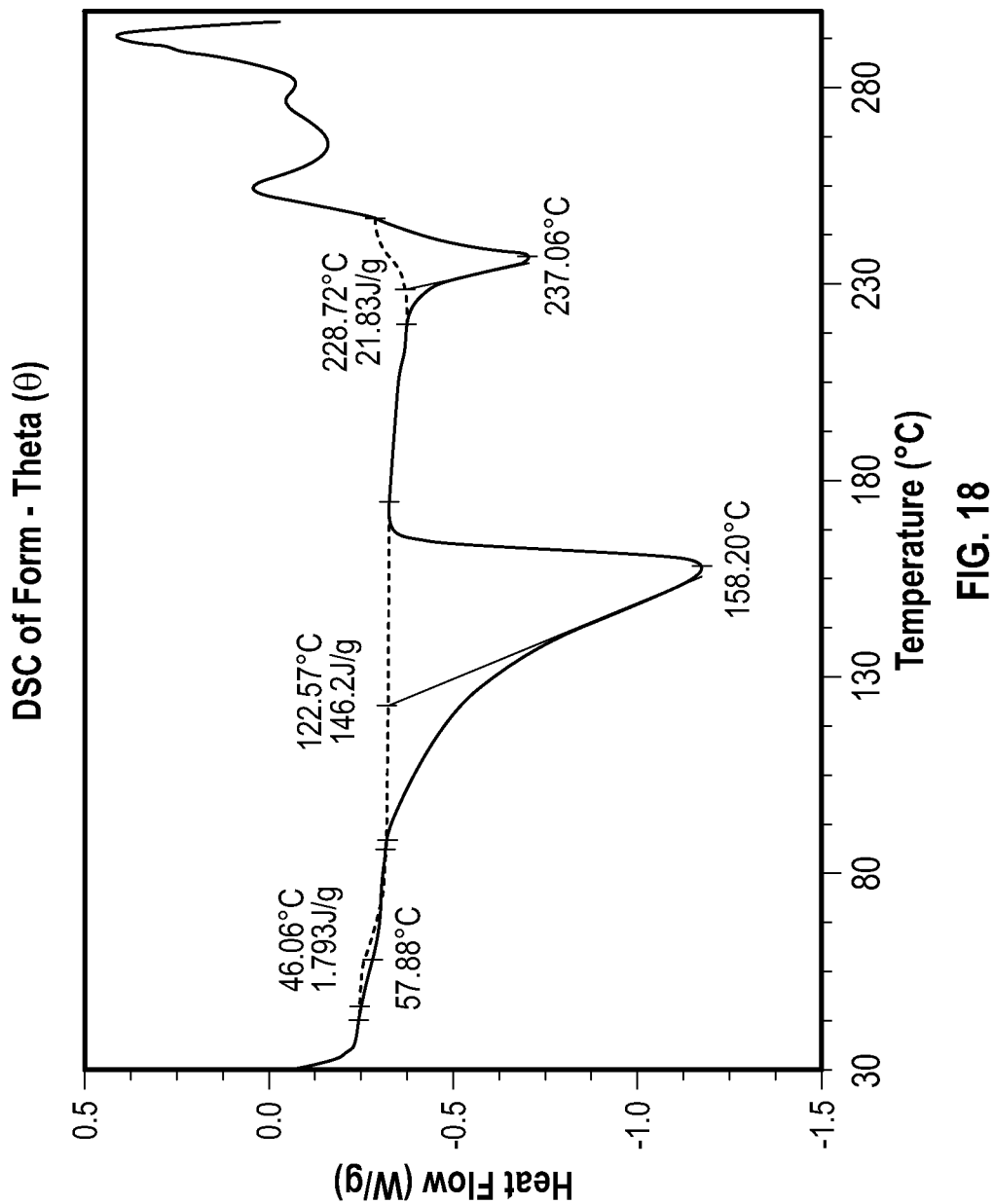
FIG. 18 is a measured differential scanning calorimetry thermogram of morphine sulfate crystalline Form θ.

7. A form of morphine sulfate according to claim 1, wherein:

Form α is characterized by a differential scanning calorimetry pattern substantially as shown in FIG. 11;

Form β is characterized by a differential scanning calorimetry pattern substantially as shown in FIG. 12;

Form γ is characterized by a differential scanning calorimetry pattern substantially as shown in FIG. 13;

Form δ is characterized by a differential scanning calorimetry pattern substantially as shown in FIG. 14;

Form ε is characterized by a differential scanning calorimetry pattern substantially as shown in FIG. 15;

Form ζ is characterized by a differential scanning calorimetry pattern substantially as shown in FIG. 16;

Form η is characterized by a differential scanning calorimetry pattern substantially as shown in FIG. 17; and Form θ is characterized by a differential scanning calorimetry pattern substantially as shown in FIG. 18.

8. A composition comprising at least one Form of morphine sulfate according to claim 1.

9. The composition according to claim 8, wherein the composition is a pharmaceutical composition further comprising at least one pharmaceutically acceptable excipient.

10. A method of treating pain comprising administering a pharmaceutical formulation according to claim 9 to a subject in need thereof.

11. A method of making morphine sulfate Form α according to claim 1, comprising exposing a starting material comprising morphine free base to acetone and an acid at a temperature in the range of about 20 to 26° C. for a time sufficient to yield morphine sulfate Form α.

12. A method of making morphine sulfate Form α according to claim 1, comprising exposing a starting material comprising morphine free base to water and an acid at a temperature in the range of about 55 to 65° C. for a time sufficient to yield morphine sulfate Form α.

13. A method of making morphine sulfate Form β according to claim 1, comprising exposing a starting material comprising morphine free base to isopropyl acetate and an acid at a temperature in the range of about 20 to 26° C. for a time sufficient to yield morphine sulfate Form β.

14. A method of making morphine sulfate Form γ according to claim 1, comprising exposing a starting material comprising morphine free base to acetone and an acid at a temperature in the range of about 55 to 65° C. for a time sufficient to yield morphine sulfate Form γ.

15. A method of making morphine sulfate Form δ according to claim 1, comprising exposing a starting material comprising morphine free base to ethanol and an acid at a temperature in the range of about 20 to 26° C. for a time sufficient to yield morphine sulfate Form δ.

16. A method of making morphine sulfate Form ε according to claim 1, comprising exposing a starting material comprising morphine free base to methanol and an acid at a temperature in the range of about 20 to 26° C. for a time sufficient to yield morphine sulfate Form ε.

17. A method of making morphine sulfate Form ζ according to claim 1, comprising exposing a starting material comprising morphine free base to water and an acid at a temperature in the range of about 20 to 26° C. for a time sufficient to yield morphine sulfate Form ζ.

18. A method of making morphine sulfate Form η according to claim 1, comprising exposing a starting material comprising morphine free base to an ethanol/methanol mixture and an acid at a temperature in the range of about 20 to 26° C. for a time sufficient to yield morphine sulfate Form η.

19. A method of making morphine sulfate Form θ according to claim 1, comprising exposing a starting material comprising morphine to water and an acid at a temperature in the range of about 65 to 75° C. for a time sufficient to yield morphine sulfate Form θ.

\* \* \* \* \*